United States Patent [19]

Wagner et al.

[11] 4,038,198

[45] July 26, 1977

[54] STORAGE STABLE MULTICOMPONENT MIXTURES USEFUL IN MAKING AMINOPLASTS, PHENOPLASTS, AND POLYURETHANES

[75] Inventors: Kuno Wagner, Leverkusen-Steinbuechel; Karlheinz Andres, Cologne, both of Germany

[73] Assignee: Bayer Aktiengesellschaft, Leverkusen, Germany

[21] Appl. No.: 571,133

[22] Filed: Apr. 24, 1975

[30] Foreign Application Priority Data

May 7, 1974 Germany .............................. 2421987

[51] Int. Cl.$^2$ .................... C08G 18/30; C08G 18/34; C08G 18/38; C09K 3/00
[52] U.S. Cl. .................. 252/182; 260/2.5 AB; 260/51.5; 260/67.6 R; 260/69 R; 260/77.5 AB
[58] Field of Search .................. 252/182; 260/2.5 AB, 260/77.5 AB, 2.5 AM, 77.5 AM

[56] References Cited

U.S. PATENT DOCUMENTS

| | | | |
|---|---|---|---|
| 3,663,465 | 5/1972 | Fogiel | 260/2.5 AB |
| 3,758,444 | 9/1973 | Wagner et al. | 260/32.4 |

FOREIGN PATENT DOCUMENTS

| | | |
|---|---|---|
| 1,321,583 | 6/1973 | United Kingdom |
| 1,322,774 | 7/1973 | United Kingdom |
| 1,345,001 | 1/1974 | United Kingdom |

OTHER PUBLICATIONS

Encyclopedia of Polymer Technology (vol. 10) (Wiley), (N.Y.), (1969), pp. 488–489.

*Primary Examiner*—Donald E. Czaja
*Assistant Examiner*—H. H. Fletcher
*Attorney, Agent, or Firm*—Gene Harsh; Joseph C. Gil; William E. Parry

[57] ABSTRACT

The present invention relates to storage stable multicomponent mixtures containing:
a. at least one compound selected from the group consisting of lactams and aza lactams;
b. at least one compound selected from the group consisting of water, and difunctional acid-group-free organic compounds containing functional groups selected from the group consisting of hydroxyl, primary amino-, secondary amino, and sulfhydryl groups; and
c. at least one acid selected from the group consisting of
   i. mono- and poly-carboxylic acids,
   ii. organic and inorganic acids of phosphorus,
   iii. inorganic acids of boron, and
   iv. partially hydrolyzed antimonous and antimonic acid esters of polyhydroxyl compounds with molecular weights of from 62 to 600.

13 Claims, No Drawings

STORAGE STABLE MULTICOMPONENT MIXTURES USEFUL IN MAKING AMINOPLASTS, PHENOPLASTS, AND POLYURETHANES

BACKGROUND OF THE INVENTION

Low-viscosity solvent-free reactive systems have acquired an increased commercial significance in the manufacture of plastics in view of present ecological requirements and since they tend to conserve both energy and solvents.

It has been proposed to use molten ε-caprolactam (m.p. 70° C.) as a solvent for substantially insoluble compounds of relatively high molecular weight such as polymethylene thioureas, optionally together with non-reactive organic hydroxyl-group-free solvents, such as aromatic hydrocarbons, acetone, ethers, esters, tetrahydrofuran and aliphatic halogenated hydrocarbons (see, e.g. German Pat. No. 910,336).

It has also been proposed to use lactam mixtures or associates of water, alcohols, polyalcohols, oximes, amines and diamines for a variety of different applications as non-reactive or reactive solvents, for the production of foams, cellular and non-cellular polyurethane plastics, catalysts, mold release agents, and the like. (Belgian Pat. Nos. 775,907; 776,906; 803,215; 784,735; and 803,214; German Offenlegungsschriften Nos. 2,330,211 and 2,357,191; and U.S. Pat. No. 3,578,444.)

It is known that a variety of different cyclic amides (such as butyrolactam, valerolactam and ε-caprolactam) form highly viscous salt-like or crystallized salts with concentrated, anhydrous acids (such as sulfuric acid and hydrohalic acid) (cf. Houben-Weyl, Methoden der Organischen Chemie, Vol. 11/2, page 552 (1958). In addition, these products are readily hydrolyzed with aqueous acids at elevated temperature to form the corresponding salts of the amino carboxylic acids (Houben-Weyl, supra, page 565).

In view of (1) the fairly marked tendency of lactams unsubstituted on the nitrogen to hydrolyze in the presence of acids; (2) the high viscosity of the salt-like compounds; and (3) their tendency to form salts through the formation of crystallizing salts of amino carboxylic acids or of salts of any amino polyamides formed, lactam mixtures or associates (e.g., of the type described in Belgian Pat. Nos. 776,906 or 776,907, such as those prepared from 1 mol of ε-caprolactam and 1 to 4 mols of polyhydroxyl compounds, monoalcohols or water in the presence of inorganic acids or organic mono- or poly-carboxylic acids) had been expected to be unstable mixtures which, in view of their poor storability, excessive viscosity, and corrosion behavior, would give rise to significant disadvantages when used on a commercial scale.

DESCRIPTION OF THE INVENTION

It has now been surprisingly found that three-component lactam mixtures which are stable, solvent-free, low viscosity reactive systems may be obtained by blending (a) a lactam-type compound, (b) an acid free compound selected from the group consisting of water and organic compounds containing at least two groups containing active hydrogen groups, and (c) an inorganic or organic acid. Component (a) is preferably selected from the group consisting of lactams, aza lactams and mixtures thereof. Component (b) is preferably selected from the group consisting of water and difunctional acid-group-free organic compounds wherein the functional groups are selected from the group consisting of hydroxyl, primary amino-, secondary amino, and sulfhydryl groups.

The novel mixtures of the instant invention provide preparative organic chemistry with fundamentally new possibilities when used as a reactive media as will be disclosed hereinafter.

As noted above, the compositions disclosed herein are storage stable, multicomponent mixtures containing:
a. at least one lactam-type compound, said compound preferably selected from the group consisting of lactams and aza lactams;
b. at least one acid-group-free compound, said compound preferably selected from the group consisting of water and difunctional acid-group-free organic compounds containing functional groups selected from the group consisting of hydroxyl, primary amino-, secondary amino-, and sulfhydryl; and
c. at least one organic or inorganic acid, said acid preferably selected from the group consisting of
  i. mono- and poly-carboxylic acids,
  ii. organic and inorganic acids of phosphorus,
  iii. inorganic acids of boron, and
  iv. partially hydrolyzed antimonous and antimonic acid esters of polyhydroxyl compounds with molecular weights of from 62 to 600.

Component (a) of the mixtures of the instant invention is a lactam-type compound, preferably selected from the group consisting of lactams and aza lactams, and, most preferably, corresponding to the general formula:

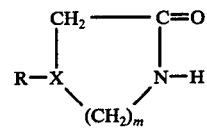

wherein
m represents an integer of from 0 to 9, and
X represents nitrogen or a CH-group; provided that when X represents nitrogen,
R represemnts a saturated aliphatic hydrocarbon radical having 1 to 6 carbon atoms or an araliphatic hydrocarbon radical having 7 to 10 carbon atoms, and provided that when X represents a CH-group, R represents hydrogen.

Examples of suitable lactams and aza lactams of this type include butyrolactam, ε-caprolactam, dodecalactam, 1-N-methyl hexahydro-1,4-diazepine-3-one, 1-N-benzyl hexahydro-1,4-diazepine-3-one and mixtures thereof. The presently preferred compound is ε-caprolactam.

Component (b) of the mixtures of the instant invention is an acid-group-free compound, preferably selected from the group consisting of water and difunctional acid-group-free organic compounds containing functional groups selected from the group consisting of hydroxyl, sulfhydryl, primary amino and secondary amino. Preferably these materials have molecular weights of from 60 to 250.

Apart from water, it is particularly preferred to use as component (b), an alcohol corresponding to the general formula R(OH)$_n$ wherein
R represents a saturated aliphatic hydrocarbon radical having 2 to 40 preferably 2 to 6 carbon atoms, which radical may optionally be interupted by ether-oxygen atoms; and wherein
n represents an integer from 2 to 8, are preferably either 2 or 3.

Examples of such alcohols include ethylene glycol, 1,2-propane diol, 1,3-propane diol, 1,2-butane diol, 1,4-butane diol, 1,6-hexane diol, 1,18-octadecane diol, glycerol, trimethylol propane, trimethylol ethane, diethylene glycol, dipropylene glycol, triethylene glycol, tripropylene glycol, oxethylated saccharose, oxethylated or propoxylated glucose or erythritol, and the like. These compounds may also be present in admixture in the mixtures according to the invention.

Other materials which may be used as component (b) of the instant invention include polyfunctional compounds containing hydroxyl, sulfhydryl and/or amino groups of the type described in German Offenlegungsschriften Nos. 2,062,288 and 2,062,289 and in Canadian Pat. No. 948,193 or British Pat. No. 2,382,588, the disclosures of which are herein incorporated by reference.

Component (c) of the mixtures of the instant invention is an organic or inorganic acidic compound or compounds.

As hereinbefore indicated, one type of suitable acidic compound are (i) mono- and poly-carboxylic acids. Such acids may be saturated or unsaturated. Further, such acids may be substituted with either non-reactive groups such as halogen atoms or dialkylamino groups or with reactive groups such as hydroxyl groups. Suitable acids of the above type include formic acid, acetic acid, propionic acid, butyric acid, isobutyric acid, crotonic acid, chloroacetic acid, dichloroacetic acid, glycolic acid, cyanoacetic acid, chloropropionic acid, lactic acid, oxalic acid, malonic acid, succinic acid, adipic acid, fumaric acid, maleic acid, malic acid, tartaric acid, citric acid, benzoic acid, toluic acid, phenylactic acid, chlorobenzoic acid, nitrobenzoic acid, hydroxybenzoic acid, aminobenzoic acid, phthalic acid, terephthalic acid, acrylic acid, methacrylic acid, crotonic acid, stearic acid, oleic acid, linoleic acid, glutaric acid, pimelic acid, azelaic acid, sebacic acid, itaconic acid, hydroxybutyric acid, ricinoleic acid, thioglycolic acid, isophthalic acid, coconut oil fatty acid, linseed oil fatty acid, hydroxyacetic acid, maleic acid semi-esters with monohydric alcohols, dimethylamino acetic acid, dimethylolpropionic acid, and the like. Suitable hydroxy-containing carboxylic acids further include reaction products of polycarboxylic and anhydrides such as maleic acid anhydride, phthalic acid anhydride, tetrahydrophthalic acid anhydride or hexahydrophthalic acid anhydride, with polyols of the type referred to above in the description of component (b). The presently preferred carboxylic acids are those of the type which show a tendency towards acylating reactions and towards anhydride formation through condensation and/or which, in addition to the acid function, contain at least one other reactive group.

Another type of suitable acidic compound are (ii) organic and inorganic acids of phosphorus. Suitable examples of such acids include phosphorous acid, phosphoric acid, pyrophosphoric acid, polyphosphoric acid, methane phosphonic acid, benzene phosphonic acid, dodecane phosphonic acid, 4-dimethylamino benzene phosphonic acid, 2-phenyl ethylene phosphonic acid and the corresponding phosphorous acids. Also suitable are the acid semi-esters of the above-mentioned inorganic and organic acids of phosphorous with polyalcohols having molecular weights of from 62 to 600.

Yet another type of suitable acidic compound are (iii) inorganic acids of boron including orthoboric acid, metaboric acid, tetraboric acid and the like.

Finally, the acidic compound used herein may be (iv) a partially hydrolyzed antimonous or antimonic acid ester of a polyhydroxyl compound with a molecular weight of from 62 to 600. Such esters may be formed e.g., by reacting antimonous or antimonic acid alkyl esters (alkyl = methyl, ethyl, propyl and/or butyl) with said polyhydroxyl compounds e.g., glycerol, trimethylolpropane at 20°-80° C using 1-5 mols of polyhydroxyl compound per mol of ester and subsequently contacting the reaction product with 1-2 mols of water at room temperature.

When inorganic acids are used, it is preferred that those of the type which may be converted into polymeric acids by the removal of water, i.e., by polycondensation, be used. Examples include orthoboric acid, phosphorous acid, phosphoric acid, and the corresponding polyacids such as pyrophosphoric acid, polyphosphoric acid and polybasic acids.

Similarly, when organic acids are used, it is preferred that those of the type which slow a tendency towards acylating reactions and towards anhydride formation through condensation and/or which, in addition to the acid function, contain at least one other reactive group be used.

The mixtures of the instant invention may, of course, contain mixtures of the above-mentioned acids.

The mixtures of the instant invention generally contain from 0.5 to 8 mols of component (b), and from 0.5 to 10 mols of component (c) per mol of component (a). Preferably the compositions of the instant invention contain from 1 to 4 mols of component (b), and from 1 to 8 mols of (c) per mol of component (a).

The mixtures of the instant invention are generally prepared by mixing the components at temperatures of from 0° to 100° C., preferably at temperatures of from 20° to 80° C. and most preferably, at temperatures of from 30° to 60° C. To prepare the lactam mixtures disclosed herein, components (a), (b) and (c) may be mixed in any order. If the lactam-type compound is initially mixed with the organic or inorganic acid, a binary system is apparently formed in which the following equilibria presumably prevail:

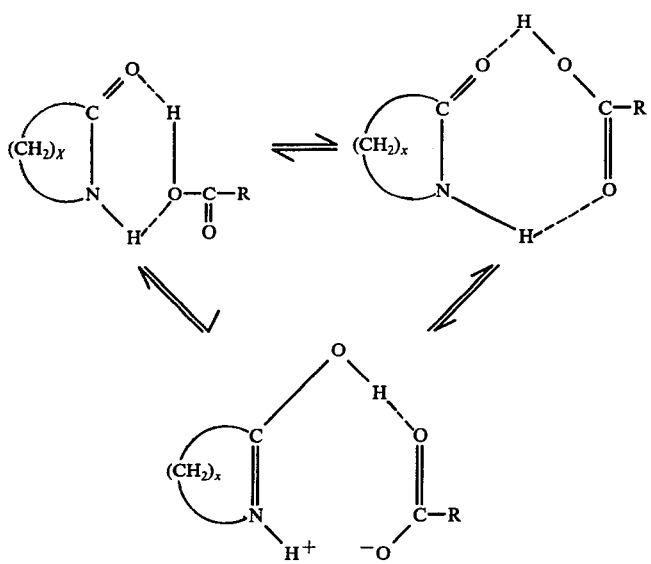

It is particularly surprising in this respect that even strong acids such as formic acid (R = H) or oxalic acid (R = COOH), neither lead to the splitting of the lactam ring nor to the formation of substantially insoluble salts.

The three component mixtures according to the invention are generally of low-viscosity and are stable in storage at from 20° to 50° C. The exact structure of the composition formed by mixing the components as described above is not known with certainty. The storability and viscosity properties of the mixtures according to the invention remain unaltered even when they contain up to 10 mols of inorganic or organic acid per mol of lactam-type compound.

As indicated above, it is not possible to make any definite statements as to the exact structures of the mixtures of the instant invention. However, the mixtures according to the invention are generally storable liquids with viscosities of from 10 to 20,000, and preferably from 12 to 8000, cP at 20° C. in which (by virtue of their suitability as a reactive and, at the same time, powerfully dissolving reaction medium) a variety of different chemical reactions may be carried out. In particular, polyaddition, polycondensation and polymerization reactions may be carried out in the mixtures of the instant invention, resulting in the formation of interesting, often highly fireproof plastics, porous absorbents and ion exchangers.

One surprising aspect is the discovery that, for example, extremely low-viscosity and storable mixtures or salt-like solutions of 1 mol of ε-caprolactam, approximately 0.5 to 1.5 mols of trimethylol propane and approximately 0.5 to 1.5 mols of formic acid, said mixtures generally corresponding to the formula:

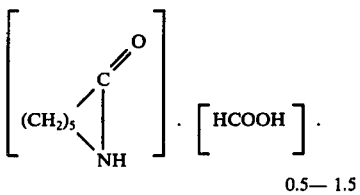

-continued

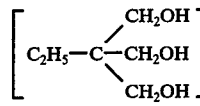

represent, in relation to polyisocyanates, extremely interesting, anhydrous reactive systems with a strong blowing effect. They are in the form of completely solvent-free, reactive liquids which release large quantities of $CO_2$ and CO as blowing agents in isocyanate reactions. This particular reaction gives high molecular weight polyurethane polyureas branched through biuret groups, the entire ε-caprolactam being combined with the heavily branched polyurea-polybiuret polyurethanes formed with terminal and lateral NCO-groups of the macromolecule to form corresponding urea groups. In formal terms, the formic acid present represents masked water (Semi-esters of oxalic acid have a similar effect in the mixtures.) During the reaction with isocyanates, it yields 1 mol of $H_2O$ and, in addition, 1 mol of carbon monoxide [HCOOH → $H_2O$ × CO]. Accordingly, multicomponent reactions of this type may be controlled in such a way that the low-viscosity, reactive mixtures may be quantitatively converted, in the absence of solvents, into cellular plastics, the blowing agent (CO and $CO_2$) being formed continuously and non-spontaneously from formic acid and isocyanate, so that uniform foam formation is possible.

Another surprising discovery is the mechanism by which, for example, liquid ε-caprolactam-$H_2O$-formic acid or glycerol or trimethylol propane mixtures react with polyisocyanates at temperatures above 120° C. This mechanism involved the following idealized reactions, which, in the interest of clarity, are depicted as involving only two components:

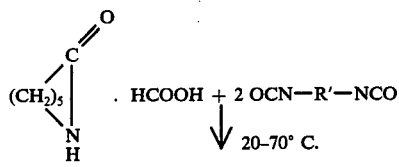

a)

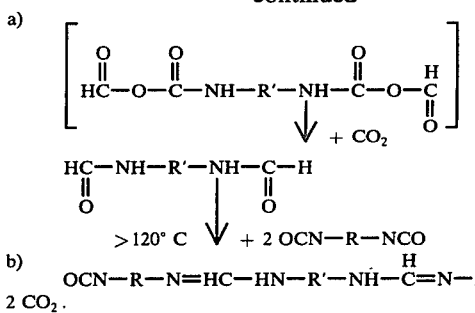

b) OCN—R—N=HC—HN—R'—NH—C=N—R—NCO + 2 CO$_2$.

Strongly basic polyfunctional amidines are formed in the reaction in the presence of the third component (H$_2$O, polyalcohols). Such amidines have a polymerizing effect on excess diisocyanate or tend towards cycloadditions by the NCO-group reacting with the amidine group to form 1:1 or 1:2 cycloadducts, the NCO-groups of the macromolecule only being broken off by caprolactam residues in the final stage by addition of the less reactive ε-caprolactam.

Accordingly, the mixtures herein result in a surprisingly vigorous exothermic reaction with a high heat balance which enables "high-rise" reactions to be carried out with isocyanates, resulting in the formation of foams or cellular foam sheets or coatings which, by virtue of the favorable heat balance lose their tackiness extremely quickly.

Another new, interesting and fast reaction is the formation of cellular polyurethane-polyamide foams which are formed when, for example, a liquid mixture of 2 mols of ε-caprolactam, 1 mol of formic acid, 1 mol of 1,4-butane diol and 1 mol of adipic acid are reacted with a polyisocyanate, resulting in the formation of plastics which, in addition to polyurethane groups and

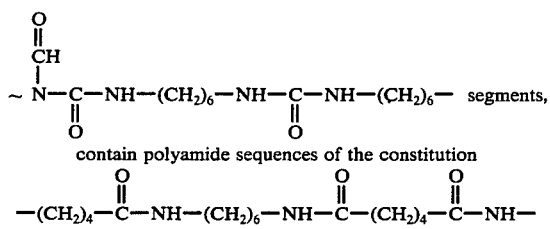

contain polyamide sequences of the constitution $$—(CH_2)_4—\overset{O}{\overset{\|}{C}}—NH—(CH_2)_6—NH—\overset{O}{\overset{\|}{C}}—(CH_2)_4—\overset{O}{\overset{\|}{C}}—NH—$$

Another particularly surprising aspect is the possibility of using strongly acidic, but nevertheless readily foamable mixtures, which are liquid at room temperature. A specific example includes the following:

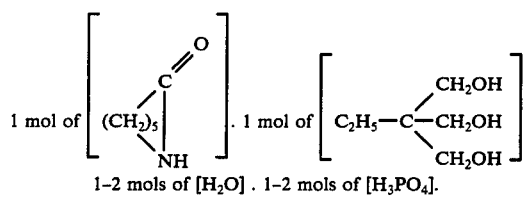

1-2 mols of [H$_2$O] . 1-2 mols of [H$_3$PO$_4$].

It is surprising that mixtures of this type may be mixed or emulsified very effectively with polyisocyanates, often in the absence of emulsifiers, the lactam content presumably being responsible for emulsification. Another particularly surprising factor is the discovery that the foam formed does not have any acidity as a result of the fact that phosphoric acid is reacted to form built in, relatively high molecular weight, water-insoluble polyphosphates and polyphosphate phosphoric acid amides. Even after repeated extraction with cold water, it is not possible to detect any free phosphoric acid in the aqueous extract.

This discovery of the incorporation of phosphoric acid through polycondensation reactions to form built in or incorporated polyphosphoric acids is totally unexpected, because, in a comparison test conducted in the absence of lactams at from 20° to 40° C., there is no reaction at all between phosphoric acid and polyisocyanates, while at temperatures above 80° C. only polyureas and water-soluble low molecular weight pyrophosphoric acid are formed.

Foams produced, for example, from 1 mol of ε-caprolactam, 1 mol of trimethylol propane, 2 mols of water and 1 mol of o-phosphoric acid are highly flameproof. It is thus readily possible to obtain foams containing incorporated polyphosphate or polyphosphate polyester phosphoric acid polyamides.

Hitherto, it has not yet been possible to use phosphoric acids in foamable systems without serious disadvantages (British Pat. Nos. 919,067 and 1,056,360). In the formation process of the foam there has been a danger of complete or partial collapse. Additionally, the foaming reaction is undesirably decelerated to a considerable extent. Additionally, the foams obtained have shown faults in the form of bubbles and cracks and, for the most part, only contain soluble, free phosphoric acid with the result that they have readily undergone degradation. The major advantage of using the storable mixtures according to the invention is that phosphoric acid and phosphorous acid may be processed and incorporated in the polyurethane in much higher concentrations. Accordingly, the phosphorus content of the new foams may be increased from a level of from 1.2 to 1.4% to a level of from 6 to 10%.

Another surprising factor is that it is possible to obtain foams of high lactam content without any difficulties. ε-caprolactam is a monofunctional chain-terminating compound and, for this reason, should interfere seriously with the formation of high molecular weight, crosslinked foams. In the mixtures according to the invention, however, water and polyol, and water releasable from phosphoric acid during polyphosphate formation, react much more quickly than ε-caprolactam in relation to polyisocyanates, so that completely crosslinked polyurea-polybiurets of extremely high molecular weight are formed. The lactam which reacts only in the end phase is merely incorporated for terminating lateral branches in the macromolecules.

Accordingly, the formation of crosslinked polyaddition products with the following constitution by reacting polyisocyanates with liquid associates of 1 mol of ε-caprolactam, 1 mol of trimethylol propane, 1 mol of water and 1 mol of orthophosphoric acid takes place in the following idealized form:

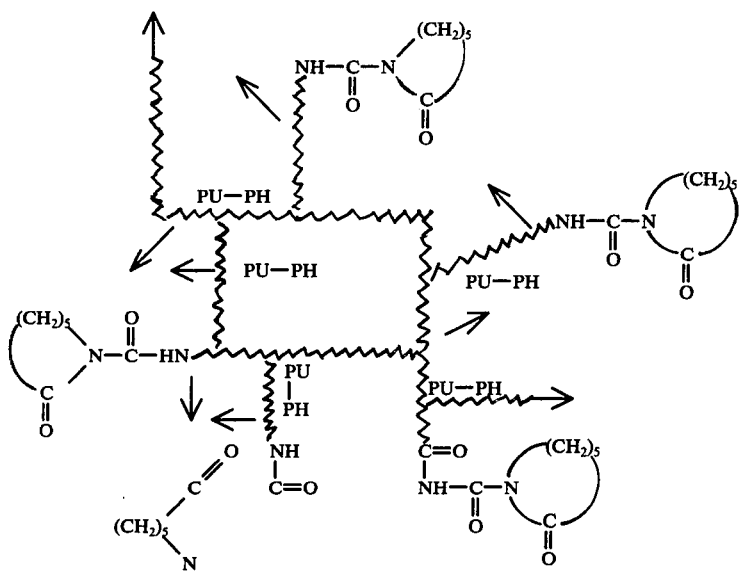

wherein
PU-PH represents polyurethane polurea segments with incorporated polyphosphate and
← represents biuret branches.

The growing biuret branches indicated by arrows are ultimately broken off in the final phase of the reaction by ε-caprolactam. Although ε-caprolactam is a monofunctional compound with respect to NCO-reactions, the formation of high molecular weight, completely crosslinked polyaddition products is thus not prevented and, in view of the high degree of branching and crosslinking of the macromolecules formed, large quantities by weight of ε-caprolactam may be incorporated into the macromolecule.

Since there are no free amino or hydroxyl groups in a heavily crosslinked and branched macromolecule of this type, the lactam group cannot be subsequently eliminated by a split-off reaction. The

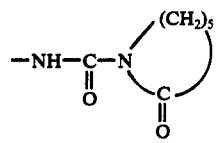

groups incorporated have the thermal stability of biuret groups. Even at 170° C, ε-caprolactam cannot be removed from the highly crosslinked polyaddition products or from the foams obtained in the absence of NH₂— or OH-groups.

Mixtures of (a) 1 mol of ε-caprolactam, 1 mol of trimethylol propane, 1 mol of water and 1 mol of phosphorous acid; (b) 1 mol of ε-caprolactam, 1 mol of water and 1 mol of orthoboric acid; and, (c) 1 mol of ε-caprolactam, 1 mol of trimethylol propane, 0.5 mol of phosphoric acid and 0.5 mol of boric acid, behave similarly. With these mixtures, all the reactive components are converted into solid polyaddition products during the foaming reaction, accompanied by the elimination of $CO_2$ only, i.e., no other volatile substances or solvents are eliminated.

Another particularly surprising factor is the discovery that large quantities of phosphoric or boric acid may be used for controlling NCO-polyadditions which, hitherto, have always been extremely dangerous, resulting in spontaneous inflammation and extremely serious nuclear combustion. This is possible since in the presence of lactams, the highly exothermic isocyanate reaction is accompanied by an endothermic polyphosphate-forming reaction. As a result, considerable quantities of the exothermic NCO-heat are consumed enabling foaming reactions to be carried out with extremely high NCO:OH concentrations in the foamable mixture.

By using the multicomponent mixtures of the invention, and more especially those containing phosphoric acid, and/or boric acid, optionally in admixture with acrylic acid, methacrylic acid and copolymerizable vinyl monomers, for the production of foams, it is possible, without any danger whatever, to carry out totally unexpected reactions involving solvent-free multicomponent reactive system which, in the past, it has not been possible to carry out on a commercial scale. Thus, it is not possible even today, despite refined technologies, to dissipate the large quantities of heat given off during spontaneous reactions of low molecular weight reactants, for example in accordance with the following reaction scheme:

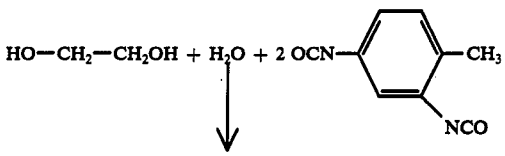

polyurethane polyureas + about 48 Kcal, safely, in a matter of minutes, without dilution with relatively high molecular weight polyhydroxyl compounds which provide for moderate hydroxyl concentrations in the foamable mixture, because the intense heat effect of the above reaction (approximately 48 Kcal) gives rise to spontaneous decompositions and spontaneous inflammation. Conventional foaming recipes can, to some extent, handle the dissipation of heat from foamable mixtures containing approximately 10 g, at the most 18 g, of NCO per 100 g of foamable mixture both in the case of hard foams and, to a certain extent, in the case of soft foams as well. By foaming the multicomponent mixtures according to the invention, it is now surprisingly possible to react foamable mixtures containing as much as 30 to 40 g of NCO per 100 g of foamable multicomponent mixtures without any danger of spontaneous reactions, spontaneous inflammation or risk of explosions during the foaming process. This possibility is attributable to the fact that, due to the presence of increased quantities (for example, from 2 to 8 mols) of o-phosphoric acid or boric acid, an endothermic reaction consuming large quantities of heat takes place in the presence of lactams through polyphosphate, pyrophosphate or polyborate formation, approximately 8 Kcal per mol being consumed in the formation of one pyrophosphate bond. Accordingly, up to 4 Kcal of heat per mol of $H_3PO_4$ may be absorbed by the endothermal condensation of 2 mols of $H_3PO_4$ by reaction according to the invention.

The principle of heat "destruction" by endothermal polycondensation is of particular significance in cases where, in addition to the NCO-reactions, highly exothermic polymerization or copolymerization reactions are carried out, with multicomponent mixtures containing, for example, acrylic acid, maleic acid semi-esters containing hydroxyl groups, styrene, vinyl acetate, acrylonitrile, acrylic, methacrylic acid esters and the like. In the process according to the invention, safe processes, greatly reduced in their heat balance by endothermic reactions, are also promoted by the fact that the free acids or acid semiesters of phosphoric acid, boric acid or, if desired, sulphuric acid ensure that, in the case of isocyanate reactions, even extremely high-energy reactions only begin at moderate speed by virtue of the acidity of the systems, with the result that casting times and coating times of up to 5 minutes may be attained. This is generally long enough for a variety of different molding processes, spread-coating processes, spraying processes, and coating processes to be conveniently carried out. These longer processing times are a distinct contrast to the processing times of only a few seconds normally encountered in conventional foam-producing processes.

For substantially quantitative polyphosphate or polyborate formation where the reactive multicomponent mixtures are used in the production of foams containing polyurethane or polyurea and, optionally, polycarbodiimide groups, it is necessary to use at least two NCO-equivalents per mol of lactam and at least two NCO-equivalents per mol of phosphoric acid or boric acid. In general, steps should also be taken to ensure that, during the reaction, temperatures of about 140° to 185° C. either prevail in the foam or are achieved by briefly heating the foam.

Another potential application of the mixtures of the instant invention is in the production of extremely brittle foams containing polyurethane-polyurea-polybiuret-polyphosphoric acid amide or polyboric acid amide segments. Heavily cross-linked foams of this type may be converted into finely-divided powders simply by applying gentle pressure. This eliminates the need for expensive grinding operations and produces interesting, heavily cross-linked powders which may be used with advantage for filling chromatography columns; as non-tacky and non-caking adsorbents for numerous heavy metals, such as copper, mercury, iron, calcium and barium; and as decolorizing aqueous dye solutions. Particularly interesting foams with a high incorporated phosphorus and boron content are obtained especially in cases where temperatures of from 170° to 180° C. are reached during the foaming process, which is readily possible without any danger of spontaneous inflammation or nuclear combustion in the resulting foams (note, e.g., Example 9).

Particularly brittle foams with favorable adsorption properties are obtained from the mixtures herein especially in cases where the mixtures used either consist solely of lactams, water and acids, such as phosphoric acid, boric acid, or of mixtures which consist of lactams, low molecular weight triols, such as trimethylol propane or glycerol, water and acids, such as phosphoric acid, boric acid, maleic acid semi-ester, acrylic acid, methacrylic acid. [The molar ratio of components in the four-component mixture being 1:1:1:1 (based on $\epsilon$-caprolactam, triol, water, acid)].

In cases where multicomponent mixtures according to the invention containing low molecular weight polyols and inorganic or organic acids are used, other parallel endothermic reactions, such as esterification and anhydride-forming reactions and even sulphonation reactions (where mixtures containing sulphuric acid are used at temperatures above 120° C.) may of course also occur.

The use of the multicomponent mixtures disclosed herein also enables mixtures of the type containing from 2 to 10% by weight of 30% hydrogen superoxide solution as weak acid to be safely foamed. In this case, radical reactions, urethane-forming reactions, decarboxylation reactions, the formation of azo compounds, oxidation reactions and, in the presence of monomeric vinyl compounds, polymerization, copolymerization and grafting reactions, take place during foaming, in particular on the active methylene groups of 4,4'-diisocyanato-diphenylmethane and in the $\alpha$-position to aliphatic and cycloaliphatic polyisocyanates. This particular application of the multicomponent mixtures in foaming reactions with aromatic isocyanates does of course result in the formation of foams brown to yellow in color through the formation of foams containing incorporated azo dyes.

Another particular advantage is that multicomponent mixtures containing from 1 to 3 mols of phosphoric acid, homogeneously absorb large quantities of highly concentrated aqueous urea solutions. When used in high concentrations, urea is an effective flameproofing agent which reduces the evolution of smoke gas from foams and, in accordance with the invention, may be used in homogeneous solution for foaming reactions, again utilizing endothermic polyphosphate formation or polyborate formation.

The same applies relative to methylolated ureas, trimethylol melamine, methylolated dicyanodiamides, and other nitrogen-rich compounds which, in combination with polyphosphates, considerably improve the flameproof properties of the foams obtained. Low molecular weight bis-urethanes, methylolated low molecular weight bis-amides, bis-urethanes, and tri-urethanes may also be used and are obtained in conventional manner, for example, by reacting low molecular weight polyalcohols with urea as isocyanic acid donor at temperatures of from 140° to 180° C.

In the multicomponent mixtures according to the invention which may be used, for example, for isocyanate foaming reactions, from 0.5 to 10 mols of phosphoric acid, or boric acid, may be used per mol of lactam, optionally in admixture with other organic or inorganic acids. The preferred range is from 1 to 8 mols of o-phosphoric acid or boric acid per mol of lactam. In cases where foams produced with very large quantities of phosphoric acid still contain acid constituents, such as phosphoric acid, pyrophosphoric acid or oligomeric phosphoric acids, the free acids may readily be converted into ammonium phosphates or ammonium polyphosphates after production of the foam or after the production of powdered foams by reacting acid phosphates or free NCO-groups with gaseous ammonia on and in the interconnecting cell arms of the foams in the form of a matrix reaction by the process described in German Offenlegungsschrift No. 1,953,347. The quantity of the mixtures used depends upon the required density of the foam and upon the required degree of crosslinking in such a way that the ratio of the equivalents of water, hydroxyl groups, lactam and, optionally, amino groups to the equivalents of the polyisocyanate is from 0.5:1 to 1.5:1.0, and preferably from 0.8:1.0 to 1.4:1.0. If desired, however, it is also possible to use an extremely large excess of isocyanate, for example of up to 600%, especially in cases where catalysts producing carbodiimide groups or isocyanurate groups are used (See, e.g., Belgian Pat. No. 657,835 or German Pat. Application No. P 20 44 192.3). Catalysts known to have an outstanding carbodiimideforming capacity are, for example, phospholines, phospholine oxide, phospholidines and phospholidine oxides. Examples include 1-phenyl-3-phospholine, 3-methyl-1-phenyl-3-phospholine, 3-methyl-1-phenyl-3-phospholine-1-oxide and 1-methyl phospholine-1-oxide. Catalysts with a high isocyanurate-forming capacity include alkali salts of organic carboxylic acids, alkali alcoholates, condensation products of phenol or polynuclear polyphenols with formaldehyde and dimethylamine such as 2,4,6-trisdimethylaminomethylphenol, and relatively high molecular weight condensates of bisphenol A, formaldehyde and dimethylamine.

New types of foams may also be produced with particular advantage from ε-caprolactam mixtures containing unsaturated hydroxy carboxylic acids of the type which may be obtained in a wide range by the addition of polyalcohols, preferably diols and triols, to unsaturated carboxylic acid anhydrides, for example maleic acid anhydride. Such materials are produced as follows:

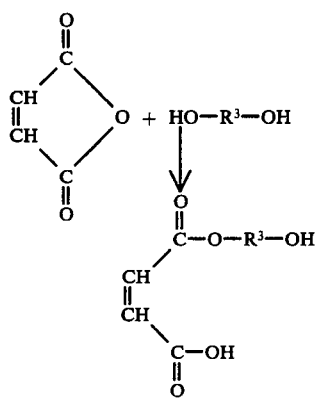

wherein $R^3$ represents a polyfunctional radical of a polyol with a molecular weight of from 62 to 600, and wherein the maleic acid radical may also be repeatedly bonded to the alcohol component, for example, to trimethylol propane:

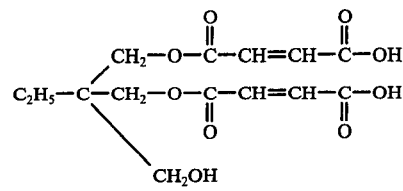

Mixtures of semi-esters containing free hydroxyl and carboxylic acid groups, for example of maleic acid anhydride with diethylene glycol, gylcerol, trimethylol propane, pentaerythritol, saccharose, glucose, with the associates according to German Offenlegungsschrift No. 2,062,288, for example, with the associate of 1 mol of ε-caprolactam and 1 mol of trimethylol propane, are particularly interesting both as such and in admixture with one mol of orthophosphoric acid or phosphorous acid. Mixtures of this type may be favourable reacted in the presence of radical formers using polyisocyanates containing large quantities by weight of copolymerizable monomers such as styrene. The polymerization is greatly enhanced by the heat generated during the isocyanate reaction. The products so formed contain the styrene in bonded form to a hitherto unobtainable extent. Foams of this type may be crosslinked to form polyamide groups. In addition, they may contain in the macromolecule, cyclic or crosslinking carboxylic acid anhydride groups, since the action of isocyanates on carboxylic acids always results in the formation of anhydride structures in a proportion of 20 to 30%, in addition to the preferential polyamide formation. However, it is also possible in this particular process to use vinyl monomers which do not copolymerize to the extent of styrene, but preferentially form homopolymers instead. The heat effect may be intensified by increasing the NCO/OH concentration. Vinyl acetate, styrene + vinyl acetate, α-methyl styrene, acrylic acid, methacrylic acid, methacrylamide, methacrylamide methylol methyl ether, acrylic acid-β-hydroxyethyl ester, acrylic acid methyl ester, methylmethacrylate and methacrylic acid hydroxy propyl ester, may be converted as homopolymers into cellular solids by the intense heat generated by the low molecular weight foamable mixtures, resulting in the formation of cellular two-phase plastics.

If 2 to 3 mols of o-phosphoric acid are used per mol of ε-caprolactam, it is possible with aromatic polyisocyanates for example to produce readily pulverizable powders suitable for chromatography columns. After brief after-treatment with dilute calcium or barium hydroxide solutions, highly cross-linked polyaddition products are obtained.

It is also possible to produce columns of foam containing ammonium polyphosphates and powdered, highly cross-linked adsorbents, for example from the vinyl polymers and foams containing polyphosphoric acid groups and, optionally, free phosphoric acids, in the form of matrix reactions of the type described in German Offenlegungsscrhift No. 1,953,347, by simple gassing with ammonia, hydrazine or ethylene diamine.

Among the group of aforementioned hydroxy carboxylic acids, however, semi-esters of oxalic acid, such as:

HO—CH₂—CH₂—O—CH—O—CO—CO—OH

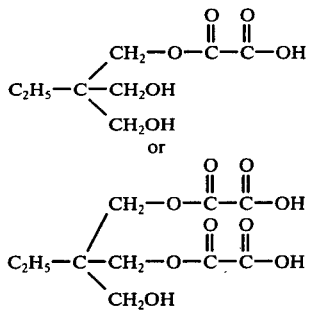

are also suitable for mixture formation and subsequent foaming, since, by reacting with polyisocyanates to form polyamide in a secondary reaction, they additionally yield $CO_2$ or CO as blowing agent.

Another interesting solvent-free system for the production of new types of foams is the mixture obtained from 1 mol of ε-caprolactam, 1 mol of trimethylol propane, 1 mol of acrylic acid, 1 mol of water and 1 mol of orthophosphoric acid. The intense heat effect accompanying foam formation results in extensive, additional cross-linking of the foams at 185° C as a result of incipient thermal polymerization of the acrylamide derivatives formed.

Another interesting aspect of the present invention is the discovery that it is possible to control the viscosity of the mixtures described herein within wide limits using small quantities of diamines or hydrazines. Thus, sudden increases in viscosity may be induced with 0.1 mol of hydrazine hydrate, 0.1 mol of trimethylhexamethylene diamine, 0.1 mol of 1-aminomethyl-1,3,3-trimethyl-5-aminocyclohexane (=isophorone diamine), 0.1 mol of ethylene diamine, 0.1 mol of trimethylamine, or 0.1 mol of permethylated triethylene tetramine of dimethylbenzylamine, thus enabling flow properties and unit weights to be controlled during subsequent foaming, especially in the production of highly cross-linked powders designed for use in preparative chromatography. In addition, the amine salts formed in the associate mixtures have a catalytic effect during the blowing reaction, although the system as a whole is still strongly acid. A variety of different polyketimines, of the type described in U.S. Pat. Nos. 3,743,667 or 3,770,799 and used as starting products for modifying reactions, for example hydroxy alkylation reactions, may also be mixed with the mixtures without the formation of any salt-like deposits. Other advantageous compounds are polySchiff's bases, for example of isobutyraldehyde and hexamethylene diamine, 1,5,11-triaminoundecane, trimethyl hexamethylene diamine and isophorone diamine.

Another interesting property of the mixtures containing phosphoric acid and phosphorous acid in particular is their dissolving power for a number of N-methylol compounds in the urea, melamine, dicyanodiamide, bis-urethane or polyamide series and methylolated phenol series. Despite the high reactivity of the methylolated aminoplast precondensates or phenoplast precondensates, the high concentration of phosphoric acid promotes the formation of semi-esters of the methylol compounds with, for example, phosphonic acid which may be directly used in soluble form for the isocyanate reaction. By applying this combination, it is possible to greatly increase non-flammability and, while saving isocyanate, to initiate simultaneous aminoplast condensation and formaldehyde crosslinking. Accordingly, the mixtures described herein enable dimethylol urea, dimethylol thiourea and trimethylol melamine, which are completely insoluble in all polyisocyanates, to be incorporated into a variety of different foams according to the invention via the stage of highly reactive semi-esters of phosphoric acid in accordance with the following idealized reaction scheme:

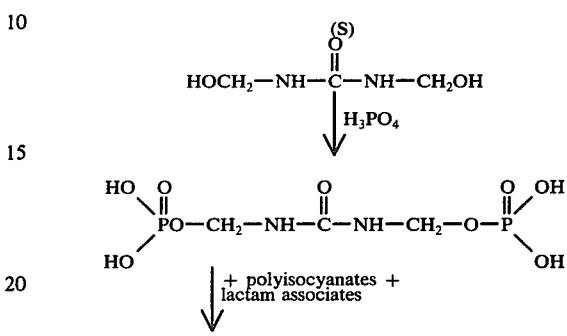

HIGHLY CROSS-LINKED POLYURETHANE-POLYPHOSPHORIC ACID AMIDEPOLYBIURET FOAMS

The foams according to the invention with a high degree of incorporated polyphosphate and, if desired, free phosphoric acid content have a high binding capacity for heavy metals or heavy metal compounds from liquids or gases and a high adsorption capacity for purifying liquids, river water, industrial effluent and exhaust gasses from motor vehicles. Chromium, manganese, cobalt, nickel, copper and mercury may be bound in large quantities to the finely powdered and readily pulverizable foams. By virtue of the fact that they may be readily pulverized, the specific surface area of the foams ($m^2/g$) may be greatly increased. Their adsorption capacity may be increased by producing the foams with the mixtures of the instant invention in the presence of diatomaceous earth, pumice stone, zeolite, kaolin, alumina, silica gel, coke, active carbon, graphite or bentonite as fillers.

The non-flammability of the foams obtained may be further increased by adding to the liquid mixtures finely ground, insoluble urea oxalate, melamine phosphate, powdered methoxylated ureas, dicyanodiamide, powdered methylolated phenols, powdered crosslinked residues of phenol-formaldehyde condensates and the like.

The mixtures according to the invention, especially those based on (a) ε-caprolactam, (b) glycerol or trimethylol propane and (c)formic acid, acetic acid, isobutyric acid, hydroxy acetic acid and the like, also afford many other advantages in the field of polymerization, copolymerization and graft polymerization of vinyl monomers. They are particularly suitable for dispersing and dissolving surprisingly large quantities of hydrophobic vinyl monomers, such as vinyl chloride, vinylidene chloride, vinyl acetate, acrylic acid esters, styrene, α-methyl styrene, chlorbutadiene and the like, together with up to 50% by weight of unsaturated monomers containing hydroxyl groups, such as a acrylic acid or methacrylic acid hydroxyethyl (or methyl) ester. Polymerization may be carried out in them to form concentrated solutions or dispersions of the corresponding hydroxyl-group-containing polymers, copolymers or graft polymers in these "reactive" solvents.

On completion of polymerization, the multicomponent mixtures obtained may be immediately reacted with polyisocyanates to form cellular plastics, the carboxylic acids used generating $CO_2$-blowing gas by reacting with the isocyanates, or $CO_2$ being formed as blowing gas by initiating anhydride formation through the water initially formed.

By suitably selecting the components of the mixtures (for example the lactam components and any inorganic or organic mono- and poly-carboxylic acids, which may either be hydrophilic or hydrophobic), it is possible to prepare solvent-free reactive systems which are adapted to be reacted in such a way that compatibility between all the components of the multicomponent system is guaranteed.

Thiophosphoric acids, monoesters and diesters thereof, sulphurous acid; organic acids of sulphur and phosphorus such as phosphonic acids, sulphinic acids, dithiocarbamic acids, xanthogenic acids, sulphoxylic acids and suphamic acids; and, α-hydroxy sulphonic acids, such as hydroxy methane sulphonic acid, hydroxy ethane sulphonic acid and the like may also readily be added to the aforementioned mixtures of the ε-caprolactam to adjust viscosity ranges of from 1000 to 20,000 cP without, at the same time, producing any signs of precipitation. Stronger acids with an emulsifying effect such as di-sec.-butyl napththalenesulphonic acid, may be added to the mixtures in smaller quantities.

Semi-amides of cyclic carboxylic acids of the type which may be obtained from maleic acid anhydride, phthalic acid anhydride, hexahydrophthalic acid anhydride, methyl hexahydrophthalic acid anhydride and disubstituted monoamines such as diethylamine, di-n-propylamine and di-n-butylamine, are also interesting amide-group-containing acid components for use in the preparation of the mixtures according to the invention.

The multicomponent mixtures described herein are also interesting, solvent-free liquid reagents for use in fast reactions of the type encountered in aminoplast and phenoplast chemistry. They are especially interesting in cases where these reactions take place at high velocity, so that the formation of N-methylol lactams and bis-methylene lactams predominates [for example, in the formation of thermostable o- or p-methylolated phenols and their polycondensation products which, through chain termination (for example by esterification with the inorganic phosphoric acids present in the addition compounds), are caught at a lower condensation stage by semi-ester formation], thus avoiding crosslinking reactions. Solutions of this type of hydroxyl-group-containing phenoplasts in the mixtures according to the invention may be converted with polyisocyanates into highly flameproof cellular plastics directly, i.e., without any need for further solvents and blowing agents.

The mixtures according to the invention may also be used for the production of flameproof, porous elastomer films, or for the direct production of porous foam sheeting on textile substrates. In addition, to phosphoric acid or boric acid, these mixtures preferably contain associates of the lactams, preferably those of ε-caprolactam, with ethylene glycol, diethylene-triethylene glycol, 1,4-butane diol, 1-methyl diethanolamine or aminopropanol and water or formic acid.

Systems containing mixtures of formic acid or hydroxyl groups and free carboxylic acid groups in the same molecule, for example semi-esters of cyclic carboxylic acid anhydrides and bifunctional alcohols, especially those produced in the presence of diamine salts or hydrazine salts of oleic acid, recinoleic acid, semi-esters of cyclic carboxylic acids or amine salts of formic acid, such as:

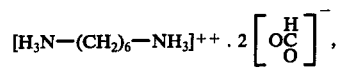

or lactam-associate mixtures with the idealized constitution:

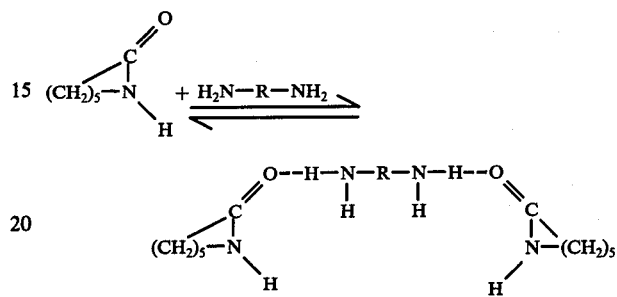

which may readily be obtained in accordance with Example 1 of German Offenlegungsschrift No. 2,117,576, are useful as chain-extending agents for the production of foamed elastomer systems, especially where α,ω-diisocyanato polyester or polyether polyurethanes (= NCO-prepolymers) are used.

The mixtures according to the invention are also interesting, solvent-free liquid reagents for use in fast epoxide polyaddition reactions. In this case, liquid ε-caprolactam-trimethylol propane-phosphoric acid mixtures, ε-caprolactam-ethylene glycol-acrylic acid mixture, or ε-caprolactam-1,4-butane diol-maleic acid semi-ester-water mixtures, optionally in admixture with ε-caprolactam-methacrylic acid, methacrylic acid-β-hydroxyethyl ester mixtures or β-caprolactam-N-methyl diethanolamine-boric acid mixtures, are reacted with compounds containing epoxide groups, preferably with commercial-grade epoxide resins of bisphenol A and epichlorhydrin or polyurethane epoxides of 1 mol of an α,ω-diisocyanato polyester or polyether urethane and 2 mols of glycidyl alcohol, in the absence of solvents to form hydroxyl-group-containing epoxy resins modified with ester or semi-ester groups, and converted with polyisocyanates into foams in a second phase. In this modified procedure, the end products obtained may be reacted in the presence of radical formers, using polyisocyanates of the type to which large quantities by weight of copolymerizable monomers such as styrene, have been added. The polyaddition and copolymerization reaction is helped along by the intense heat generated from the isocyanate reaction. Vinyl polymerization and copolymerization reactions may thus be carried out with high yields. However, it is also possible in this modification to use vinyl monomers which do not copolymerize to the extent of styrene, but instead preferentially form homopolymers. The NCO heat effect may be increased to such an extent that, vinyl acetate, styrene + vinyl acetate, α-methyl styrene, acrylic acid, methacrylic acid, methacrylamide, methacrylamide-methylolmethyl ether, acrylic acid-β-hydroxyethyl ester, acrylic acid methyl ester, methylmethacrylate and methacrylic acid hydroxypropyl ester, may be quickly polymerized under the effect of the heat given off by the low molecular weight foamable mixtures, and converted into cellular solids, resulting in the formation of cellular two-phase plastics.

By virtue of their high dissolving power, it is possible to add to the multicomponent mixture of the invention, polyhydroxyl compounds of relatively high molecular weight, especially in cases where the mixtures are to be used for the production of foams, porous sheets and porous coatings of high elasticity and reduced brittleness. The following polyhydroxyl compounds are preferably used for this purpose: Compounds with at least two hydrogen atoms capable of reaction with isocyanates and, generally, with a molecular weight of from 400 to 10,000. Included are compounds containing amino groups, thiol groups, hydroxyl groups or carboxyl groups. Compounds of this type which are preferred are polyhydroxy compounds and more especially compounds containing from 2 to 8 hydroxyl groups, especially those with a molecular weight of from 800 to 10,000 (preferably from 1000 to 6000). Examples include polyesters, polyethers, polythioethers, polyacetals, polycarbonates, polyester amides containing at least two, generally two to eight and preferably two to four hydroxyl groups, of the type known for the production of homogeneous and cellular polyurethanes.

Representatives of the types of compounds useable are described, for example, in High Polymers, Vol. XVI, "Polyurethanes, Chemistry and Technology", by Saunders-Frisch, Interscience Publishers, New York, London, Vol. I, 1962, pages 32 to 42 and pages 44 to 54, and Vol. II, 1964, pages 5 to 6 and 198 to 199, and in Kunststoff-Handbuch, Vol. VII, Vieweg-Hochtlen, Carl-Hanser-Verlag, Munich, 1966, pages 45 to 71.

Starting organic isocyanates suitable for use in the foaming reactions of the multicomponent mixtures according to the invention include essentially any organic polyisocyante such as aliphatic, cycloaliphatic, araliphatic, aromatic and heterocyclic polyisocyanates of the type described, for example, by W. Siefgen in Justus Liebigs Annalen der Chemie, 562, pages 75 to 136.

In many cases, water and/or readily volatile organic substances may be used as blowing agents in the production of foams from the multicomponent mixture of the instant invention.

Catalysts suitable for use in the production of the foams are the known catalysts including tertiary amines, organotin compound, nitrogen-containing bases, tetra alkyl ammonium hydroxides, alkali hydroxides such as sodium hydroxide, alkali phenolates such as sodium phenolate, and alkali alcoholates such as sodium methylate.

It is also possible to use surface-active additives (emulsifiers and foam stabilizers), cell regulators such as paraffins or fatty alcohols or dimethyl polysiloxanes, pigments, dyes and flameprofing agents.

The multicomponent mixtures described herein can be reacted by the known single-state process, by the prepolymer process or by the semi-prepolymer process. In many cases machines of the type described, for example, in U.S. Pat. No. 2,764,565, are used. Particulars of processing equipment suitable for use in accordance with the invention may be found, for example, on pages 121 to 205 of Kunststoff-Handbuch, Vol. VI, published by Vieweg and Hochtlen, Carl-Hanser-Verlag, Munich, 1966.

The solvent-free liquid multicomponent mixtures of the invention may be used for the following purposes, inter alia. in the production of hard-elastic porous plastics, plastics powders, porous sheets and porous coatings with a high degree of non-flammability; in the production of polyphosphate-modified biuret, allophanate and isocyanurate isocyanates, and for epoxy polyaddition reactions coupled with NCO crosslinking reactions with endothermic polyphosphate formation; multicomponent mixtures based on $H_3PO_4$, acrylic acid, methacrylic acid and, in particular OH-group-containing, readily available maleic acid semi-esters copolymerizable with styrene, may be used for NCO-reactions in which the intense heat of reaction is dissipated through polyphosphate and polyborate formation; in the production of phenoplast or aminoplast solutions esterified with phosphoric acid or boric acid on terminal methylol groups and subsequently foamed with endothermic polyphosphate formation; in high-solids systems for the production of porous, flameproof coatings on synthetic or natural textiles by the reactive process; multicomponent mixtures containing hydrogen superoxide may be used for safe faoming and combined NCO-polyaddition, vinyl polymerization and graft polymerization accompanied by endothermic polyphosphate formation; in the production of extremely brittle foams, readily pulverized under light pressure, with a high adsorption capacity for mercury, calcium, strontium and lead; in the production of light-stable polyurethane-polyamide foams; for the production of finely dispersed fillers and metal powders and for their foaming and for dissipating the heat of reaction through parallel endothermic polyphosphate or polyborate formation; for the production of foamable, dispersed or dissolved vinyl polymers; and, for solvent-free aminoplast and phenoplast condensation and for the solvent-free modification of epoxy resins.

As indicated hereinbefore, the structure of the compositions herein is not known with certainty. Thus, the term, "mixtures", as used herein is meant to describe the compositions in whatever form they may be present such as equilibrium product, salt, hydrogen-bonded addition products, or the like.

The parts quoted in the following Examples are parts by weight unless otherwise stated. The invention is further illustrated by these Examples.

EXAMPLE 1

Liquid, crystallized or molten lactams in quantities of 1 mol are dissolved at from ambient temperature to 60° C with the hydroxyl-group-containing compounds listed in Table 1 to form liquid lactam mixtures, and the resulting solutions are subsequently blended at from 15° to 65° C with the carboxylic acids listed in Table 1. Even where crystallized ε-caprolactam melting at 70° C is used, storable liquids, at from 20° to 35° C are obtained in every case without any insoluble polyamide salts or acrylamides of the lactams being formed over a test period of 4 months. The multicomponent mixtures obtained have the remarkably low viscosities as cited in Table 1:

TABLE 1

| Sample No. | Lactam Component | OH-Component | Acid Component | Molar ratio | $\eta$(cP) at 20° C |
|---|---|---|---|---|---|
| 1 | (CH₂)₅ caprolactam ring (C=O, NH) | $H_2O$ | HCOOH | 1:1:1 | 12.4 |
| 2 | " | $HO-CH_2-CH_2OH$ | HCOOH | 1:1:1 | 14.8 |
| 3 | " | $H_2O$ | $CH_2=CH-COOH$ | 1:0.5:1 | 18.5 |
| 4 | " | $H_2O$ | $CH_2=C(CH_3)-COOH$ | 1:0.5:1 | 19.3 |
| 5 | " | $H_2O$ | $CH_3-CH_2-C(=O)-OH$ | 1:1:1 | 55 |
| 6 | " | $H_2O$ | $HO-CH_2-C(=O)-OH$ | 1:0.5:1 | 320 |
| 7 | " | $H_2O$ | $HS-CH_2-C(=O)-OH$ | 1:0.5:1 | 250 |
| 8 | " | $H_2O$ | $HS-CH_2-C(=O)-OH$ | 1:1:1 | 218 |
| 9 | " | $HO-(CH_2)_4-OH$ | oleic | 1:1:1 | 34 |
| 10 | " | $H_2O$ | $CH_3-(CH_2)_4-CH(C_2H_5)-C(=O)-OH$ | 1:0.5:1 | 7.5 |
| 11 | " | $HO-CH_2-CH_2OH$ | ricinoleic | 1:1:1 | 85 |
| 12 | " | $HO-(CH_2)_4-OH$ | $C_6H_5-COOH$ | 1:1:1 | 25 |
| 13 | " | $HO-CH_2-CH_2-OH$ | o-hydroxymethylbenzoic acid | 1:1:1 | 400 |
| 14 | " | $H_2O$ | $ClCH_2COOH$ | 1:1:1 | 12.5 |
| 15 | " | $HO-CH_2-CH_2-OH$ | maleic acid mono(2-hydroxyethyl) ester | 1:0.5:1 | 1200 |
| 16 | " | $HOCH_2-CH(CH_3)-OH$ | maleic acid mono(4-hydroxybutyl) ester | 1:0.5:1 | 1380 |
| 17 | " | $HO-(CH_2)_4OH$ | hexahydrophthalic acid mono(4-hydroxybutyl) ester | 1:1:1 | 1280 |
| 18 | " | $HO-(CH_2)_4-OH$ | phthalic acid mono(4-hydroxybutyl) ester | 1:1:1 | 2580 |

TABLE 1-continued

| Sample No. | Lactam Component | OH-Component | Acid Component | Molar ratio | $\eta$(cP) at 20° C |
|---|---|---|---|---|---|
| 19 | " | $H_2O$ | HOOC—CH=CH—COO—$(CH_2)_4$—OH | 1:0.5:1 | 1350 |
| 20 | " | $H_2O$ | HOOC—CH=CH—COO—$(O—CH_2—CH_2)_2$—OH | 1:0.5:1 | 1530 |
| 21 | " | $H_2O$ | HOOC—CH=CH—COO—$(O—CH_2—CH_2)_3$—OH | 1:0.5:1 | 1410 |
| 22 | " | HO—$CH_2$—$CH_2$OH | $HO(CH_2)_4O$—CO—CH=CH—CO—OH | 1:1:1 | 1555 |
| 23 | " | HO—$CH_2$—$CH_2$—OH | $HO(CH_2$—$CH_2$—$O)_2$—CO—CH=CH—CO—OH | 1:1:1 | 1730 |
| 24 | " | $HOCH_2CH_2OH$ | $HO(CH_2CH_2$—$O)_3$—CO—CH=CH—CO—OH | 1:1:1 | 1824 |
| 25 | " | $H_2O$ | HOOC—CH=CH—COO—$(CH_2)_4$—OH · $H_3PO_4^+$ | 1:1:1:1 | 4104 |
| 26 | " | $H_2O$ | HOOC—CH=CH—COO—$(O$—$CH_2$—$CH_2)_3$OH · $\overset{+}{H}_3PO_4$ | 1:1.5:1:1 | 5620 |
| 27 | " | $H_2O$ | HOOC—CH=CH—COO—$(CH_2)_4$—OH · $\overset{+}{H}_3PO_3$ | 1:1:1:1 | 3890 |
| 28 | " | $H_2O$ | HOOC—CH=CH—COO—$(CH_2)_3$OH · $\overset{+}{H}_3PO_3$ | 1:1:1:1 | 3540 |

EXAMPLE 2

Mixtures are initially prepared from the parts by weight quoted below of ε-caprolactam and water and/or polyalcohols by initially mixing the following components (in accordance with the procedure of German Offenlegungsschrift Nos. 2,062,289 or 2,062,288) and subsequently adding orthophosphoric acid.

Batches of 113 parts by weight (= 1 mol) of crystallized ε-caprolactam melting at 70° C are mixed at from 50° to 70° C with:

a. 18 parts by weight of water (1 mol),
b. 23.4 parts by weight of water (1.3 mol),
c. 36 parts by weight of water (2 mols),
d. 54 parts by weight of water (3 mols),
e. 72 parts by weight of water (4 mols),
f. 90 parts by weight of water (5 mols),
g. 62 parts by weight of ethylene glycol (1 mol) and 18 parts by weight of water (1 mol),
h. 122 parts by weight of ethylene glycol (2 mols) and 18 parts by weight of water (1 mol),
i. 90 parts by weight of 1,4-butane diol (1 mol) and 18 parts by weight of water (1 mol),
j. 180 parts by weight of 1,4-butane diol (2 mols) and 18 parts by weight of water (1 mol),
k. 106 parts by weight of thiodiglycol (1 mol) and 18 parts by weight of water (1 mol),
l. 34 parts by weight of 1-amino-3,3,5-trimethyl-5-amino methyl cyclohexane (0.2 mol), 62 parts by weight of ethylene glycol (1 mol) and 1 mol of water,
m. 18 parts by weight of water and 5 parts by weight of hydrazine hydrate (1 mol + 0.1 mol).

1 mol of o-phosphoric acid is then stirred into each of mixtures (a) to (m) at 40° C. Liquids of relatively low viscosity are obtained in every case (a) to (m), showing outstanding mixcibility with a variety of different polyhydroxyl compounds, coupled with surprisingly favorable reactivity to monoisocyanates and polyisocyanates despite the high acidity of the solvent-free multicomponent mixtures.

The storable multicomponent mixtures have the following viscosities at 20° C:

| | |
|---|---|
| a) 190 cP | h) 360 cP |
| b) 120 cP | i) 480 cP |
| c) 75 cP | j) 500 cP |
| d) 60 cP | k) 610 cP |
| e) 44 cP | l) 1540 cP |
| f) 38 cP | m) 180 cP |
| g) 410 cP | |

EXAMPLE 3

Salt-like, extremely thin lactam-acid solutions are initially prepared by straight-forward dissolution at from 20° to 50° C, showing the viscosities quoted in Table 2:

TABLE 2

| Sample No. | Lactam Component | Parts by weight | Acid Component | Parts by weight | Molar ratio | η (cP) at 20° C |
|---|---|---|---|---|---|---|
| 1 | (CH$_2$)$_5$ with C=O and NH (caprolactam) | 113 | HCOOH | 46 | 1:1 | 16.7 |
| 2 | " | 113 | CH$_3$COOH | 60 | 1:1 | |
| 3 | " | 113 | CH$_2$=CH—C(=O)—OH | 72 | 1:1 | 23.2 |
| 4 | " | 113 | CH$_2$=C(CH$_3$)—C(=O)—OH | 86 | 1:1 | 22.5 |
| 5 | " | 113 | CH$_3$—CH$_2$—C(=O)—OH | 74 | 1:1 | 100 |
| 6 | " | 113 | HO—CH$_2$—C(=O)—OH | 76 | 1:1 | 606 |
| 7 | " | 113 | HS—CH$_2$—C(=O)—OH | 92 | 1:1 | 349 |
| 8 | " | 113 | oleic acid | 282 | 1:1 | 3.4 |
| 9 | " | 113 | CH$_3$—(CH$_2$)$_3$—CH(C$_2$H$_5$)—C(=O)—OH | 144 | 1:1 | 7.5 |
| 10 | " | 113 | ricinoleic acid | 298 | 1:1 | 395 |
| 11 | " | 113 | C$_6$H$_5$—COOH | 122 | 1:1 | 33.5/21° C |
| 12 | " | 113 | salicylic acid (OH-C$_6$H$_4$-COOH) | 138 | 1:1 | 620/30° C |
| 13 | " | 113 | Cl—CH$_2$—COOH | 95 | 1:1 | 9.4/20° C |
| Sample No. | Lactam Component | Parts by weight | Acid Component | Parts by weight | Molar ratio | η (cP) at 20 – 25° C |

TABLE 2-continued

| | | | | | | |
|---|---|---|---|---|---|---|
| 14 | (CH₂)₅ C=O NH | 113 | CH−C−O−CH₂−CH₂−OH ‖ CH−C−OH ‖ O | 160 | 1:1 | 1550/20° C |
| 15 | " | 113 | (benzene ring with)−C(=O)−O−(CH₂)₄−OH and −C(=O)−OH | 222 | 1:1 | 1780/25° C |
| 16 | " | 113 | (cyclohexene ring with)−C(=O)−O−(CH₂)₄−OH and −C(=O)−OH | 226 | 1:1 | 1635/25° C |

Storable multicomponent mixtures may then be prepared from the low-viscosity liquids of Table 2 by adding to samples 1 to 16, 1 mol of water or 1 mol of ethylene glycol; 1 mol of 1,4-butane diol; 1 mol of trimethylol propane; 1 mol of diethylene glycol; 1 mol of glycerol; from 5 to 9 mols of water and 1 mol of saccharose or glucose; or by adding from 1 to 8 mols of water and from 1 to 8 mols of phosphoric acid or 1 mol of boric acid. If from 0.1 to 1 mol of ethanolamine, N-methyl ethanolamine, triethanolamine, n-butyl diethanolamine, N-methyl dipropanolamine or one of their oxethylated or propoxylated derivatives, is added to multicomponent mixtures of this type the viscosity values may be specifically increased to levels of up to 10,000 without producing any crystalline deposits in the multicomponent mixtures.

EXAMPLE 4 a. A relatively low viscosity mixture with the idealized constitution:

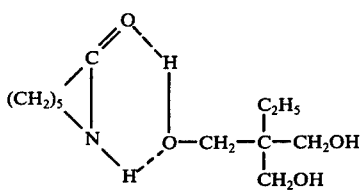

is intially prepared in accordance with German Offenlegungsschrift No. 2,062,288 by melting 1mol of ε-caprolactam (= 113 g) and 1 mol of trimethylol propane (= 134 g). This initial mixture has a viscosity of approximately 330 cP at 20° C. 1 mol of phosphorous acid ($H_3PO_3$) and 1 mol of water are then dissolved with thorough stirring at 50° C in the mixture thus prepared, resulting in the formation of a clear, low-viscosity multicomponent mixture without the formation of any substantially insoluble or highly viscous salts. The multicomponent mixture thus obtained is completely stable in storage over a period of six weeks and has a viscosity of 1800cP at 20° C.

b. The procedure is as in (a), except that 1 mol of phosphoric acid and 1 mol of water are used. A readily pourable mixture of outstanding stability with a viscosity of only 12,852 cP at 20° C is obtained. c. 98parts by weight of crystallized o-phosphoric acid are added to 247 parts by weight (1 mol) of the initial mixture formed in (a), followed by heating to about 60° C. After 30 minutes, a crystal-clear mixture with a viscosity of about 18,000 cP at 20° C is obtained without any elimination of the ε-caprolactam and without any appreciable esterification of the polyalcohol.

d. 62 parts by weight (1 mol) of crystallized boric acid are added at 60° C to 247 parts by weight (1 mol) of the initial mixture formed in (a). Dissolution is immediate. A clear mixture with a viscosity of only 714 cP at 20° C is obtained. The crystal sludge formed after several days at 20° may be reversibly converted at a temperature as low as 50° C into a thinly liquid mixture of the same viscosity.

e. If, in this example, the intial mixture of (a) is replaced by corresponding, extremely thinly liquid mixture of 1 mol of ε-caprolactam and 1 mol of ethylene glycol, 1,4-butane diol or diethylene glycol, triethylene glycol or glycerol, of the type described in German Offenlegungsschrift No. 2,062,288, mixtures with viscosities of from 300 to 700 cP at 20° C are obtained both with from 1 to 10 mols of phosphoric acid and with from 1 to 4 mols of phosphorous acid.

Without any further addition, the mixtures obtained, despite their high acidity, may be converted with polyisocyanates into cellular plastics in a smooth reaction, water formed from o-phosphoric acid through polyphosphate formation supplying the necessary blowing gas $CO_2$ by subsequent reaction with isocyanates and endothermic formation of the high-energypolyphosphates favorably consuming so much heat from the NCO OH or NCO $H_2O$ or NCO $NH_2$ reaction that polyurethane foams may be safely formed without any spontaneous violent reactions taking place.

EXAMPLE 5

Thinly liquid mixtures are initially prepared in accordance with German Offenlegungsschrift No. 2,062,289;

a) from 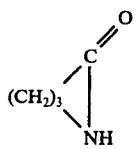

b) from 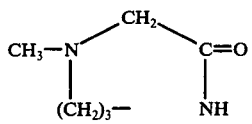

c) from 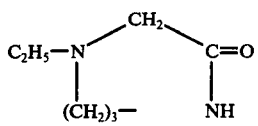

d) from 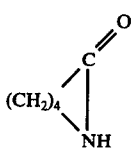

in a molar ratio of 1 : 1 with $H_2O$. 115 parts by weight of an approximately 85% orthophosphoric acid solution are subsequently added. Thinly liquid multicomponent mixtures with the following viscosities at 20° C are obtained without cleavage of the lactam rings:
a. 620 cP
b. 950 cP
c. 980 cP
d. 610 cP From 10 to 20% by weight of phenylacetic acid, p-chlorbenzoic acid, p-nitrobenzoic acid, cinnamic acid, furan carboxylic acid, maleic acid, p-methoxybenzoic acid, nicotinic acid, isonicotinic acid or anthranilic acid, may be dissolved in the mixtures thus obtained, at 70° C, resulting in the formation at room temperature of storable mixtures which may be foamed with polyisocyanates in a smooth reaction to form cellular plastics.

EXAMPLE 6

This Example demonstrates the advantageous use of the solvent-free multicomponent mixtures according to the invention as reactive systems for the production of porous, flameproofed elastic foam sheets on a textile substrate.

200 parts by weight (0.1 mol) of an adipic acid/ethylene glycol polyester with an OH number of 56 are dehydrated for 30 minutes at 120° C and subsequently reacted for 7 minutes at that temperature with 34.8 arts by weight (0.2 mol) of 2,4-tolylene diisocyanate to form the α,ω-diisocyanate prepolymer (NCO = 3.6%).

100 parts by weight of the prepolymer thus prepared, containing terminal α,ω-diisocyanate groups are stirred rapidly at 50° C with 3.42 parts by weight of a multicomponent mixture of 1 mol of ε-caprolactam, 1 mol of 1,4-butane diol, 1 mol of water and 1 mol of o-phosphoric acid, and the resulting mixture coated onto a textile substrate in the form of a cotton fabric. Surprisingly, the reactive multicomponent system has a pot life of almost 6 minutes. A coating permeated by fine pores is obtained after 12 minutes. The elimination of $CO_2$ leaves a polyurethane/polyurea film in the form of a porous sheet which, after ignition with a flame, shows self-extinguishing properties. The delayed reaction of the multicomponent mixture which is completely solvent-free enables it to be processed in novel ways, such as spread-coating, casting, calendering and impregnation over periods of up to 6 minutes, whereas solvent-free NCO-prepolymer-1,4-butane diol mixtures obtainable in accordance with the prior art lose their spreadability after only 130 seconds.

EXAMPLE 7

The procedure is exactly the same as in Example 6, except that a multicomponent mixture of 1 mol of 2-pyrrolidone, 1 mol of 1,4-butylene glycol, 1 mol of water and 1 mol of o-phosphoric acid is used. 3.25 parts by weight of the multicomponent mixture is used as chain extender for 100 parts by weight of the NCO prepolymer used in Example 5.

A cotton fabric coated with fine pores is obtained after heating for 1 hour to 160° C. The porous film obtained is flameproof. The elimination of $CO_2$ leaves a porous film of polyurethane-polyurea-polyphosphates.

EXAMPLE 8

The procedure is as in Example 6, except that the chain extender simultaneously acting as $CO_2$-blowing agent is replaced by a multicomponent mixture of 1 mol of ε-caprolactam, 1 mol of diethylene glycol, 1 mol of water, 1 mol of o-phosphoric acid, and 1 mol of boric acid, the chain extender being used in a quantity of 3.55 parts by weight. The coating obtained is completely free from phosphoric acid after heating for about 25 minutes at 150° C.

EXAMPLE 9

This Example demonstrates how the incubation time of the incipient isocyanate reactions may be advantageously prolonged by using the multicomponent mixtures according to the invention, and how, at the end of the incubation time, a vigorous but completely safe NCO reaction nevertheless takes place. This occurs even though the NCO-concentrations and OH-concentrations during the foaming process are extremely high, so that it is necessary to dissipate quantities of heat which normally could not be handled and, in most cases, would even lead to spontaneous inflammation of the foam. In the case of the process according to the invention, however, the heat generated is greatly reduced by the endothermic polyphosphate-forming reaction (amounting to around 8 Kcal per mol).

If desired, the foams obtainable in accordance with the invention may readily be pulverized and, surprisingly, are eminently suitable for absorbing lead compounds and volatile $SO_2$-vapours.

The multicomponent mixture consisting of 1 mol of ε-caprolactam, 1 mol of trimethylol propane, 1 mol of water and 1 mol of orthophosphoric acid, is used for this purpose.

36.2 parts by weight of this liquid multicomponent mixture are mixed homogeneously with 122 parts by weight of a commercial-grade polyphenyl/polymethylene/polyisocyanate, obtained by condensing aniline and formaldehyde, followed by phosgenation (31% NCO content), in the absence of emulsifiers, in the absence of a silicone stabilizer and in the absence of a catalyst accelerating the NCO reaction. The mixing time is extremely favourable, i.e., the $CO_2$-blowing effect does not begin immediately. The temperature rises slowly to 40° C only after 3 minutes 50 seconds. An extremely vigorous blowing reaction then takes place in 40 seconds, resulting in foam formation. The temperature inside the foam block has risen to 185° C after 4 minutes. It is interesting that, even after the maximum rise has been reached, the surface of the foam is still completely tack-free.

An open-cell, brittle, hard foam is obtained in which it is not possible to detect any phosphoric acid after extraction with water at room temperature. The incorporated polyphosphate fraction is more than 4% by weight, and the phosphorus content of the foam approximately 2% by weight. The foam obtained cannot be ignited even with a 400° C flame. Exposure of the foam to a hot bunsen flame merely produces carbonization. In other words, the foam is non-flammable.

The foam produced in accordance with this Example and containing incorporated polyphosphates is disintegrated simply by light, mechanical compression into porous powder particles 2 to 4 mm in diameter. 100 parts by weight of this foam powder are packed tightly into a cylindrical tube with a cross-section of 5 cm. 3 liters of water containing about 400 ppm of lead chloride are passed through the tube over a period of 6 hours. The head content of the purified water amounts to 0.6 ppm.

EXAMPLE 10

The procedure is exactly the same as in Example 9, except that the multicomponent mixture foamed contains 1 mol of phosphorous acid instead of 1 mol of phosphoric acid. Otherwise, the procedure is exactly the same as in Example 9. The advantages referred to in Example 9 in connection with production of the foams according to the invention are found in this case as well. The foam obtained, inside which a temperature of 185° C prevails after only a few minutes, shows outstanding non-flammability. At an internal temperature of 185° C, the phosphorous acid present is converted into as yet unknown incorporated compounds.

EXAMPLE 11

The procedure is exactly the same as in Example 9, except that the multicomponent mixtures consists of 1 mol of ε-caprolactam, 1 mol of trimethylol propane and 1 mol of boric acid. 30.9 parts by weight of this multicomponent mixture are mixed with 100 parts by weight of a commercial-grade polyphenyl/polymethylene polyisocyanate, obtained by condensing aniline and formaldehyde, followed by phosgenation (= 31% NCO content). No emulsifiers are required for mixing. In this case, the amount of time available for mixing is only 50 seconds. Thereafter an extremely fast blowing reaction commences; rise time: 1 minute, 10 seconds. The foam is completely tack-free after only 2 minutes and may be crushed into a fine powder by applying very light pressure. The powder is particularly suitable for filling absorber columns, and absorbs dye solutions contaminated by basic dyes. This foaming operation is accompanied by the formation at 180° C of metaborates which are incorporated into the foam and whose terminal groups in the formula:

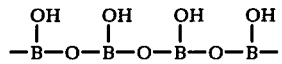

are of an as yet unknown type.

These incorporated polymetaboric acids retain Ca-Ba and Pb-ions to a remarkable extent and are also suitable for purifying aqueous solutions containing hydrogen peroxide.

EXAMPLE 12

This Example demonstrates a new, interesting isocyanate polyaddition and vinyl copolymerization according to the invention using a multicomponent mixture of 1 mol of ε-caprolactam, 0.5 mol of ethylene glycol, and 1 mol of the semi-ester formed from 1 mol of maleic acid anhydride and 1 mol of 1,4-butane diol. The heat effect of the NCO-polyaddition reaction in the presence of radical formers is entirely adequate to initiate substantially quantitative vinyl polymerization or alternating copolymerization with the maleic acid semi-ester segments, incorporated through NCO-reactions, corresponding to the formula:

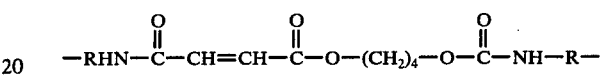

in the presence of styrene.

Foams containing polyurethane-polyamide segments and additionally crosslinked by alternating copolymerization with styrene are obtained. The blowing agent is the water added and the $CO_2$ formed by the reaction of isocyanates with the carboxylic acid, accompanied by amide formation.

30.1 parts by weight of the colorless multicomponent mixture, with a viscosity of 1.555 cP at 20° C, prepared from 1 mol of maleic acid anhydride and 1 mol of 1,4-butane diol at 70° C by ring-opening of the anhydride and subsequently adding 1 mol of ε-caprolactam and 0.5 mol of ethylene glycol, are used for this test. The mixture consists of 1 mol of ε-caprolactam and 1 mol of the semi-ester hydroxy carboxylic acid:

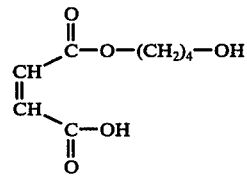

and of 0.5 mol of ethylene glycol. The mixture obtained is designated mixture (A).

A solution is prepared simultaneously consisting of 57.2 parts by weight of a tolyleene diisocyanate mixture (isomer ratio 2,4-:2,6-= 80:20) and of 30 parts by weight of styrene, 2 parts by weight of dimethylbenzylamine and 2 parts by weight of azodiisobutyronitrile (Mixture (B)).

30.1 parts by weight of multicomponent Mixture (A) are mixed with 1.8 parts by weight of water and then with Mixture (B). Foam formation begins after 90 seconds. Crosslinked foams containing hard polyamide sequences are obtained, being crosslinked with the incorporated maleic ester component through alternating copolymerization of styrene. In addition, the styrene which is not used for the alternating copolymerization is converted into polystyrene under the effect of the intense heat liberated in conjunction with NCO-polyaddition and copolymerization. Grafting reactions involving the polyurethanes and polyamides formed could also possibly occur If, in this Example, a. 20 parts by weight of acrylic acid, or b. 20 parts by weight of vinylacetate, or
c. 20 parts by weight of acrylic acid methyl ester, or
d. 20 parts by weight of methacrylic acid methyl ester, or
e. 20 parts by weight of acrylonitrile + styrene (30:70), are additionally used, the foams obtained contain crosslinked and co-laminated vinyl copolymers, i.e. multiphase solids systems, in high yields. The vinyl monomers are quickly polymerized by the internal temperature of about 185° C prevailing during foam formation.

EXAMPLE 13

The procedure is exactly the same as in Example 12 using the same multicomponent mixture, except that 10 parts by weight of a 30% hydrogen superoxide solution are added to the mixture shortly before it is added to the diisocyanate-styrene mixture. Otherwise, the procedure is as in Example 12. The high internal temperature prevailing during foaming procedures smooth polymerization and copolymerization.

The brittle, readily pulverizable foam obtained is yellow-red in color as a result of the oxidation of intermediately formed aromatic amino groups which are oxidized into azoxy groups or azo groups.

EXAMPLE 14

This Example describes the production of highly branched and crosslinked polybiuret foams with free NCO-groups. Multicomponent mixtures obtained simply from 1 mol of $\epsilon$-caprolactam, 1 mol of water and 1 mol of phosphoric acid are used for foaming. It is interesting that the foaming reaction takes place extremely slowly in this particular case.

22 parts by weight of the aforementioned mixture are foamed with 81 parts by weight of the polyisocyanate mixture used in Example 9. The foaming process is desirably retarded to a considerable extent. A vigorous $CO_2$-blowing effect is only obtained after 6 minutes 30 seconds, the temperature initially remaining below 40° C and beng increased by subsequent heating to a level of 170° C. Highly branched biuret powders with an NCO content of more than 9.5% are obtained. As insoluble powders, they may be stored indefinitely, even in moist air. They represent outstanding air filters for removing traces of amines, ammonia or hydrazine from industrial exhaust gases.

EXAMPLE 15

This Example demonstrates the use of a stable multicomponent mixture of 1 mol of $\epsilon$-caprolactam, 1 mol of trimethylol propane and 1 mol of adipic acid, which is a readily pourable liquid with a viscosity of 7267 cP at 20° C.

39.3 parts by weight of this multicomponent mixture are foamed as in Example 9 with 95 parts by weight of the same commercial-grade polyisocyanate mixture. Extremely hard foams containing polyamide sequences through the NCO/adipic acid reaction are obtained.

EXAMPLE 16

The surprisingly low viscosity of the multicomponent mixtures obtainable in accordance with the invention also enables the mixtures to be used for taking up large quantities of fillers and solid flameproofing agents in the foamable mixture without any difficulties in admixture with the polyisocyanates required for foaming, mixing times of up to 5 minutes being attainable.

Batches of 35 parts by weight of a low viscosity mixture of 1 mol of $\epsilon$-caprolactam, 1 mol of ethylene glycol, 1 mol of water and 1 mol of o-phosphoric acid are stirred with each of the following finely powdered fillers and flameproofing agents, resulting in the formation of pastes readily miscible with polyisocyanates:

a. 20 parts by weight of kaolin,
b. 25 parts by weight of red phosphorus,
c. 25 parts by weight of bentonite,
d. 35 parts by weight of ground urea (particle size 10-30 $\mu$),
e. 25 parts by weight of thiourea,
f. 22 parts by weight of powdered melamine phosphate,
g. 24 parts by weight of powdered urea oxalate,
h. 21 parts by weight of powdered calcium sulphate,
i. 28 parts by weight of powdered calcium carbonate,
j. 24 parts by weight of powdered antimony trioxide,
k. 15 parts by weight of ground cellulose powder,
l. 28 parts by weight of starch powder,
m. 30 parts by weight of carbon black,
n. 25 parts by weight of polyvinyl chloride powder,
o. 20 parts by weight of polyethylene powder,
p. 25 parts by weight of thoroughly ground graphite,
q. 30 parts by weight of ground cane sugar The pasty mixtures thus obtained are subsequently mixed homogeneously with 136 parts by weight of a commercial-grade polyphenyl/polymethylene polyisocyanate obtained by condensing aniline and formaldehyde followed by phosgenation (31% NCO-content). Although a considerable amount of heat is liberated and the NCO-concentration in 100 g of the foamable mixture is about 24.5 g of NCO, the reaction components may be mixed homogeneously over a period of 4 minutes, and sheets of hard foam with outstanding nonflammability are subsequently obtained by uniform spreading and foaming.

EXAMPLE 17

This Example shows that multicomponent mixtures of trimethylol propane or glycerol and their mono- and -bis-oxethylation products with $\epsilon$-caprolactam, N-methyl hexahydroiazepin-3-one, 2-pyrrolidone or valerolactam, in admixture with from 1 to 3 mols of phosphoric acid and from 1 to 3 mols of water, may be safely reacted with polyisocyanates, as described in Example 9, at extremely high NCO-concentrations per 100 g of foamable mixture (20 to 25 g of NCO). Endothermal, heat-consuming quantitative polyphosphate or polyphosphoric acid ester formation occurs when temperatures of about 180° C are reached during foaming or when recipes rich in phosphoric acid and water are heated to 180° C, for 30 minutes, by the application of heat following initiation of the foamng reaction. In the foaming of multicomponent mixtures very rich in water and phosphoric acid, it has proved to be of advantage to thicken the low-viscosity mixtures with organic, moderately swellable fillers and powders in order to obtain a more uniform foam.

Batches of 122 parts by weight of polyphenyl/polymethylene polyisocyanate, obtained by condensing aniline and formaldehyde followed by phosgenation (31% NCO content) are reacted with the following multicomponent mixtures, foam formation and polyphosphate formation following the pattern described in Example 9:

a. 34 parts by weight of a multicomponent mixture of 1 mol of valerolactam, 1 mol of trimethylol propane, 1 mol of phosphoric acid and 1 mol of water,
b. 30 parts by weight of a multicomponent mixture of 1 mol of 2-pyrrolidone, 1 mol of glycerol, 1 mol of phosphoric acid and 1 mol of water,
c. 36 parts by weight of a multicomponent mixture of N-methyl hexahydrodiazepine-3-one, 1 mol of water, 1 mol of phosphoric acid and 1 mol of glycerol.

EXAMPLE 18

72 parts by weight of a multicomponent mixture of 1 mol of ε-caprolactam, 2 mols of trimethylol propane, 2 mols of water and 3 mols of phosphoric acid are mixed with:
a. 35 parts by weight of cellulose powder,
b. 35 parts by weight of polyethylene powder,
c. 35 parts by weight of polyvinyl chloride powder,
d. 35 parts by weight of polyamide powder,
e. 35 parts by weight of starch powder,
f. 35 parts by weight of polyacrylonitrile powder,
g. 35 parts by weight of carbon black,
h. 20 parts by weight of cellulose powder and 15 parts by weight of copper powder,
i. 20 parts by weight of cellulose powder and 20 parts by weight of iron (III) oxide so that viscous pasts are formed. All the mixtures (a) to (i) are subsequently mixed with 270.9 parts by weight of polyphenyl polymethylene polyisocyanate (31% NCO). A good, adequate mixing time of more than 3.5 minutes is found in tests (a) to (i), although the NCO-concentration per 100 g of reactive mixture (based on reactive components without filler) amounts of about 24.5 g. The foamable mixtures may be readily poured onto metal substrates lined with an aluminum foil. Heat treatment for 15 minutes at 180° C. results in the formation of brittle, pulverizable foams which may readily be crushed into fine powder by the application of gentle pressure. The foams do not have to be ground to produce such powder. They are eminently suitable for filling chromatography columns as a non-stick, tight packing and contain approximately 7 to 10% by weight of incorporated polyphosphate. Even at temperatures as high as 200° C., these powders do not undergo spontaneous inflammation.

EXAMPLE 19

This example demonstrates the advantageous use of lactam-water-trimethylol propane-phosphoric acid mixtures for carrying out acid-catalyzed condensation reactions in phenoplast chemistry. On completion of condensation, a completely solvent-free multicomponent reactive system is obtained which may be converted with polyisocyanates to cellular plastics in a smooth reaction without any need to neutralize the acids.

222 parts by weight of 2,2-bis-(4-hydroxyphenyl)-propane are dissolved at 80° C, in 800 parts by weight of the mixture of 1 mol of ε-caprolactam, 2 mols of water, 2 mols of phosphoric acid and 1 mol of trimethylol propane, followed by the introduction, with thorough stirring, of 180 parts by weight of paraformaldehyde. Stirring for 2 hours at 85° C. gives a pourable, completely solvent-free multicomponent reactive system which contains reactive formaldehyde condensates of 2,2-bis-(4-hydroxyphenyl)-propane whose methylol groups are partially esterified with phosphoric acid and partially reacted off by condensation with caprolactam. The multi-component reactive system obtained may be reacted with 2,4-tolylene diisocyanate, with commercial-grade isomer mixtures of tolylene diisocyanates (80:20) or with 4,4'-diisocyanato diphenyl methane and polynuclear isomer mixtures of polyisocyanates of aniline-formaldehyde condensates, in accordance with Example 9 to form foams which are completely free from phosphoric acid and show outstanding non-inflammability.

EXAMPLE 20

The procedure is exactly as in Example 19, except that the 222 parts by weight of 2,2-bis-(4-hydroxyphenyl)-propane are replaced by 120 parts by weight of phenol. Completely solvent-free multicomponent reactive mixtures are obtained and are subsequently reacted with polyisocyanates, as in Example 9, to form foams with high noninflammability.

Readily foamable multicomponent systems are also obtained if, in this example, the urea is replaced by 1 mol of thiourea, dicyanodiamide, melamine, guanidine carbonate, dimethylol urea, dimethylol urea dimethyl ether, monomethylol urea, urea oxalate, malamine phosphate, trimethylol melamine, hexamethylol melamine methyl ether or by urea condensates of glyoxal (= acetylene diurein).

EXAMPLE 21

This example demonstrates the advantageous use of the mixtures according to the invention for carrying out a coupled epoxide polyaddition and polymerization which in turn leads to solvent-free pourable multicomponent reactive systems which may be reacted with polyisocyanates in a smooth reaction to form noninflammable foams.

a. 200 parts by weight of the bis-epoxide:

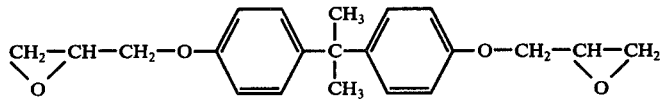

are stirred, over a period of 1 hour at 70° C. into 900 parts by weight of the mixture of 2 mols of ε-caprolactam, 2 mols of trimethylol propane, 2 mols of water, 2 mols of phosphoric acid and 1 mol of acrylic acid, resulting in partial opening of the epoxy ring and in the formation of semi-esters of phosphoric acid and unsaturated esters of acrylic acid. The readily pourable mixture may be foamed in a smooth reaction in accordance with Example 9, resulting in the formation of foams highly crosslinked both through isocyanate reactions and also through polymerization of the esterified acrylic acid at elevated temperature.

b. The mutlicomponent mixture used for the reaction with the epoxy compound described in (a) is a mixture (used in a quantity of 900 parts by weight of 1 mol of ε-caprolactam, 1 ol of the maleic acid semi-ester

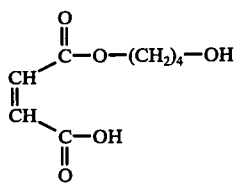

mixed with the mixture of 1 mol of ε-caprolactam and 1 mol of trimethylol propane. In other respects, subsequent reaction of the epoxy compound is carried out in exactly the same way as in (a). The readily pourable multicomponent mixture (= 30 parts by weight) may be foamed by polyaddition coupled with copolymerization in accordance with Example 9, but in the absence of oxygen and in a nitrogen atmosphere, with a mixture of 30 parts by weight of styrene containing 4 parts by weight of azodiisobutyrodinitrile and 122 parts by weight of the polyisocyanate used in Example 9. In the absence of oxygen, the intense heat effect of the NCO-polyaddition reaction results in copolymerization of the incorporated maleic acid esters with the styrene used. Highly crosslinked foams are obtained which are readily pulverized and, if desired, may be highly elasticized by the incorporation of 10 to 40% by weight of linear α,ω-dihydroxy polyethers or polyesters with an average molecular weight of 2000.

EXAMPLE 22 a. A multicomponent mixture is initially prepared by mixing (a) 1 mol of saccharose reacted with 2 mols of ethylene oxide, 8.55 mols of water (= approximately 74% oxethylated cane sugar solution with a viscosity of 626 cP/20° C) with (b) the mixture of 1 mol of ε-carprolactam, 1 mol of trimethylol propane, 1 mol of H$_2$O and 1 mol of phosphorous acid, to form a clear solution with the surprisingly low viscosity of 894 cP/20° C.

b. The procedure is exactly the same as in (a), except that that phosphorous acid is replaced by 1 mol of boric acid. $\eta_{20°C} = 1080$ cP.

c. The procedure is exactly the same as in (a), except that 2 mols of a 50% urea solution are additionally added to the multicomponent associate mixture. $\eta_{20°C} = 146$ cP.

d. The procedure is exactly the same as in (a), except that the phosphorous acid is replaced by 1 mol of orthophosphoric acid. $\eta_{20°C} = 1794$ cP.

Despite their high water content, batches of 38 parts by weight of mixtures (a), (b), (c) and (d) may be homogeneously mixed with batches of 176 parts by weight of a polyphenyl/ polymethylene polyisocyanate with a viscosity of 400 cP/20° C (NCO content 31% NCO) even in the absence of emulsifiers. The blowing reaction begins as desired after only 4 to 5 minutes, although the NCO concentration amounts to about 27.5 g of NCO per 100 g of foamable mixture. After the onset of the blowing reaction, the mixture is poured in a thin layer onto a metal dish lined with an aluminum foil. Hard, readily pulverizable, highly blown foam sheets are obtained which, after heating for 10 minutes to 180° C, do not contain any free inorganic acids. Intensive water extraction at room temperature further shows that more than 98% by weight of the sluggishly reacting, partially oxethylated saccharose was incorporated during the reaction. The readily pulverizable foam may be packed without caking in adsorption columns and shows adsorption for calcium ions, about 3 equivalents of calcium being bound per equivalent of incorporated cane sugar and incorporated phosphoric acid. The powders suitable for filling adsorption columns do not undergo spontaneous inflammation in the presence of air, even at temperatures as high as 200° C.

EXAMPLE 23

A multicomponent mixture of 1 mol of ε-caprolactam, 1 mol of trimethylol propane, 3 mols of water and 3 mols of phosphoric acid is initially prepared. Viscosity: 2333 cP/20° C. Although this reactive mixture contains more than about 45.3% by weight of phosphoric acid, 59.5 parts by weight of this mixture may be foamed with 263.3 parts by weight of a polyphenyl/ polymethylene polyisocyanate with a viscosity of 400 C°/20° C (NCO content: 31% NCO) in accordance with Example 22, resulting once again in the formation of foams which may be readily compacted in adsorber columns. By treatment with gaseous ammonia, oligomeric polyphosphates and unreacted phosphoric acids are converted by a matrix reaction into the corresponding ammonium salts which may readily be removed by subsequently washing the columns with water.

By dissolving a high polymer with a marked viscosity-increasing effect, for example, 0.5 to 20 parts by weight of water-soluble polyethylene oxide with a molecular weight of from 2000 000 to 2,000, foam formation may be stabilized. If foamable mixtures of this type are poured into glass or metal chromatography columns, fine large-surface powders may be obtained after preparation of the foam-filled columns by applying gentle pressure with a punch, i.e., without any need for excessive effort and complicated grinding operations. For producing columns of this type, the multicomponent mixtures mentioned in this Example are advantageously foamed with 20 to 30 parts by weight of cellulose powder, the cellulose being uniformly distributed during the foaming operation.

The fact that phosphoric acid may be foamed in quantities as large as this is particularly surprising because high concentrations of phosphoric acid had been expected to immediately block the stage of carbamic acid or free amine formation with the velocity of an ion reaction through which the NCO-water reaction passes, in the form of salt-like amine phosphate, which would have completely prevented foam formation. Polyphosphate-modified foam powders of this type containing up to about 10% of polyphosphate do not show any tendency towards spontaneous combination in the presence of air, even at temperatures as high as 220° C.

EXAMPLE 24

(Comparison Example to Examples 22 and 23)

If the mixtures on which Example 22 and 23 are based are prepared in such a way that no ε-caprolactam is present in the mixtures, i.e., solutions of only partially oxethylated or propoxylated saccharose, trimethylol propane, diethylene glycol and aqueous phosphoic acid are present, neither foaming nor polyphosphate formation is possible, despite the addition of arbitrary quantities of polyisocyanate. Following addition of the polyisocyanates, the temperature does not rise beyond 35° to 40° C, even after 30 minutes. CO$_2$ bubbles are merely formed on the surface of the mixtures which remain liquid. In addition, mixtures of this type cannot be adequately activated with increased quantities of basic catalysts, such as dimethylbenzylamine, potassium-, sodium formate, tin (II) octoate, and the like. Accordingly, it is not possible to produce fine powders containing foams or polyphosphates for adsorber columns.

EXAMPLE 25

This Example shows that the use in accordance with the invention of strongly acid multicomponent mixtures in contrast to conventional processes for producing polyurethane foams, makes it possible to dissipate maximum quantities of heat during foam production without any danger. It is readily possible to use foamable systems which contain as much as about 34 g/NCO per 100 parts by weight of foamable mixture. Another considerable advantage of the use of the strongly acid multicomponent mixtures in accordance with the invention is that it is possible for the first time to foam sluggishly reacting aliphatic polyisocyanates in the absence of very large quantities of tin (II) catalysts to form foams with extremely high resistance to ageing, whereas foams obtainable in accordance with the prior art from aliphatic an cycloaliphatic polyisocyanates, which have to be produced in particular in the presence of increased quantities of tin (II) and and tin (IV) catalysts, are highly susceptible to oxidation. Although, in the present Example, extremely low molecular weight reactive components are reacted in high concentration, so that the NCO concentration per 100 g of foamable mixture is extremely high, heat may readily be dissipated without giving rise to an uncontrollable, violent spontaneous reaction. Conventional foaming recipes, whether for soft foams or for hard foams, are virtually all based on NCO concentrations of at most 16.5 to 18 g of NCO per 100 g of foamable mixture.

a. 36 parts by weight of a low-viscosity mixture of 1 mol of ε-caprolactam, 1 mol of trimethylol propane, 1 mol of o-phosphoric acid and 1 mol of water are mixed with 75 parts by weight of hexamethylene diisocyanate (= 50% NCO) containing 0.2 parts by weight of a high molecular weight polyethylene oxide as viscosity-increasing agent. After 4 minutes, uniform foaming begins resulting in the formation of an elasticized, hard, light-stable foam. In this foaming operation, 100 parts by weight of the foamable mixture approximately 33.7% of NCO.

b. The procedure is as in (a) using 165 parts by weight of a low-viscosity biuret polyisocyanate which has been produced from hexamethylene diisocyanate and t.butanol in accordance with U.S. Pat. application Ser. No. 441,778, filed Feb. 12, 1974, and which has an NCO content of 23% and a viscosity of 3000 cP at 20° C. After 5 minutes, uniform foaming begins, resulting in the formation of a surprisingly highly elasticized, hard, though, light-stable foam with a weight of 80 kg/m³. Where this polyisocyanate is used, it is surprisingly even possible to foam the multicomponent mixture of 1 mol of ε-caprolactam, 1 mol of trimethylol propane, 8 or 10 mols of o-phosphoric acid and 8 to 10 mols of water with a viscosity of 1200 and 1100, without any difficulty in a uniform rise and blowing reaction. The foams obtained are free from phosphoric acid.

EXAMPLE 26

The brittle foam produced in accordance with Example 9 was size-reduced by simple mechanical compression into a fine powder with a grain size of about 1.2 mm. 30 parts by weight of the powder are introduced into a 15 mm diameter glass tube through which 5 liters of an HgCl₂ solution containing 12 ppm of Hg were passed over a period of 5 hours. Thereafter, the HgCl₂ content of the purified water only amounts to 0.8 ppm.

EXAMPLE 27

According to processes known from the literature (Houben-Weyl, Organische Phosphorverbindungen, Vol. XII/2, page 144), mixtures of acid semi-esters, mono- and di-esters of phosphoric acid are obtained by heating quantities of 1 mol of phorphoric acid with 1 mol of
  a. glycerol,
  b. trimethylol propane,
  c. oxethylated trimethylol propane (= 1 mol of trimethylol propane + 3 mols of ethylene oxide),
  d. pentaerythritol (= 1 mol of pentaerythritol + 4 mols of ethylene oxide)
for 10 hours at 110° to 140° C in a vacuum obtained using a water pump. Where glycerol is used, mixtures of

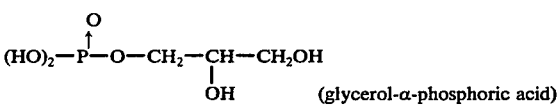
(glycerol-α-phosphoric acid)

and

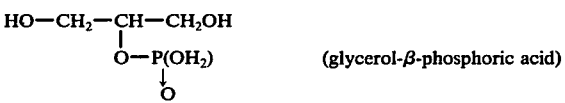
(glycerol-β-phosphoric acid)

and acid diesters

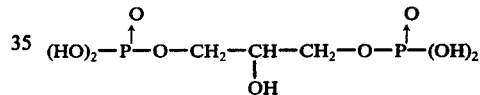

are obtained. All the acid semi-ester mixtures (a) to (d) dissolve to form clear solutions in a simultaneously prepared mixture of 1 mol of ε-caprolactam, 1 mol of trimethylol propane and 1 mol of water, the resulting solutions showing viscosities of from 2800 to 3500 at room temperature (20° C).

Similar viscosities are obtained by initially heating the polyalcohols (a) to (d) with polyphosphoric acid (= phosphoric acid dehydrated above 200° C), resulting once again in the formation of acid semi-esters and diester mixtures through cleavage of the anhydridic phosphorus-oxygen-phosphorus bond. These acid semi-ester and di-ester mixtures are mixed with the multicomponent mixture of 1 mol of ε-caprolactam, 1 mol of trimethylol propane and 1 mol of water.

The acid multicomponent mixtures are found to have similar viscosities in cases where the phosphoric acid ester mixtures are replaced by phosphorous acid mono-ester, acid diester and phosphorous acid dialkyl ester mixtures of the type obtained from components (a), (b), (c) and (d) by heating for 10 hours at 140° C with dimethyl phosphite or triethyl phosphite.

The multicomponent mixtures obtained from (a), (b), (c) and (d) may be reacted with polyisocyanates in the same way as in Example 9 to form foams with increased flame-proof properties.

EXAMPLE 28 a. 0.5 mol of 4-dimethylamino benzene phosphonous acid, b. 0.5 mol of 2-phenyl ethylene phosphonic acid,
c. 0.5 mol of 1-aminoethane-1,1-diphosphonic acid with the constitution

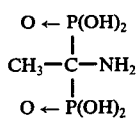

are dissolved at 60° C in separate batches of the relatively low-viscosity mixture of 1 mol of ε-caprolactam, 1 mol of glycerol and 1 mol of water. Foamable mulicomponent mixtures are obtained with the following viscosities at 30° C:
a. 250 cP
b. 230 cP
c. 175 cP.

EXAMPLE 29

Quantities of 1 mol of boric acid, boric acid anhydride or metaboric acid are heated to 100° C under a vacuum of 100 Torr with 1 mol of
a. glycerol,
b. trimethylol propane,
c. 3 mols of ethylene oxide-oxethylated trimethylol propane,
d. 2 mols of propylene oxide-propoxylated trimethylol propane, and the temperature maintained at from 95° to 105° C for 4 hours while water is removed. In addition to boric acid esters, several different compounds are formed, such as

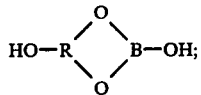

compounds with four-valent boron, such as

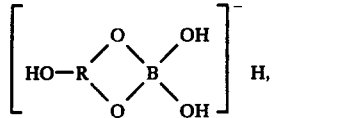

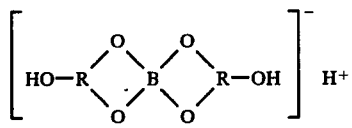

and 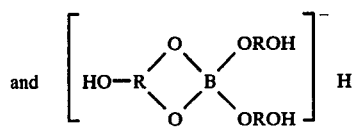

(cf.Houben-Weyl, Vol. VI/2, Sauerstoffverbindungen, page 221.)

In the above formulae, R represents the radical of the polyalcohols (a) to (d) abstracted by three OH-groups.

Separate quantities of the mixture of 1 mol of ε-caprolactam, 1 mol of glycerol and 1 mol of water, are added to these acidic boric acid mixtures. Storable multicomponent mixtures with viscosities in the range from 1800 to 2500 at 28° C are obtained. The multicomponent mixtures obtained from (a), (b), (c) and (d) may be foamed with polyisocyanates as described in Example 9 to form brittle polyurethane foams which may readily be pulverized and are suitable for use as adsorption columns and chromatographic columns. If the ε-caprolactam component is missing from from mixtures of this type, the polyol components cannot be foamed.

EXAMPLE 30

Glycerol/antimonous acid ester or antimonic acid ester mixtures in which the cyclic ester component is unknown are initially prepared, in the absence of moisture, from 3 mols of anhydrous glycerol by transesterification at 50° C/14 mm Hg with 1 mol of antimonous acid tributyl ester (a) or antimonic acid pentaethyl ester (b), the butanol or ethanol formed during the reaction being removed. Distilled, anhydrous ε-caprolactam is initially added to these moisture-sensitive esters at 50° C, a clear solution being obtained through associate formation with the numerous free hydroxyl groups. 1 mol of water is quickly stirred into mixtures (a), and (b) at room temperature, resulting in the formation of multicomponent mixtures which contain the antimonous acid monoester and diester mixtures (a) and also mixtures of glycerol partially esterified with antimonic acid.

The multicomponent mixtures obtained from (a) and (b) may be reacted with polyisocyanates in accordance with Example 9 to form readily pulverizable foams with increased flameproof properties.

EXAMPLE 31

The biuret-forming and allophanate-forming reactions summarized in this Example using multicomponent mixtures of
a. 1 mol of ε-caprolactam, 1 mol of water and 1 mol of o-phosphoric acid, and
b. 1 mol of ε-caprolactam, 1 mol of trimethylol propane, 1 mol of water and 1 mol of phosphoric acid, and an excess of commercial-grade tolylene diisocyanate mixtures, show that both biuret-forming and allophanate-forming reactions with the multicomponent mixtures according to the invention proceed completely differently from the prior art, being accompanied by additional, hitherto unknown intense catalytic effects from the polyphosphates or polyphosphoric acid amides formed, and resulting in the formation of highly functional polyisocyanates with an increased carbodiimide content.

A. 31 parts by weight of the multicomponent mixture of 1 mol of ε-caprolactam, 1 mol of water and 1 mol of o-phosphoric acid are added dropwise over a period of 2 hours at 100° C to 522 parts by weight of a commercialgrade tolylene diisocyanate (48.1% NCO, 2,4-/2,6-isomer ratio 80:20) at a stirring speed of 1000 r.p.m. The velocity of the reaction is followed by measuring the amount of $CO_2$-gas given off with a gas meter. 4.2 liters of $CO_2$ are given off after 2 hours, while about 5.5 liters of $CO_2$ are released after stirring for another hour. The solution of the biuret polyisocyanate mixture formed in monomeric tolylene diisocyanate has an NCO content of 42.1% NCO. Calculated $CO_{-2}$ formation without polyphosphate formation: approximately 2.98 liters of $CO_2$. Accordingly, water has been additionally formed through polyphosphate formation at as low as 100° C and has resulted in an increase of 5.5 - 2.98 liters = 2.52 liters of $CO_2$. The polyphosphates and polyphosphoric acid amide-polyisocyanates formed are partly dissolved and partly dispersed in the mixture. The temperature is then increased to 140° C, approximately 1.5 liters of $CO_2$ having been formed after 2 hours through continuing carbodiimide formation. Following an increase in temperature to 180° C, another 7.2 liters of $CO_2$ are formed in only 20 minutes. The reaction product is quickly cooled, giving a highly viscous ε-caprolactam modified biuret polyisocyanate mixture containing approximately 16% by weight of carbodiimide group and 25% of NCO which, by virtue of its increased viscosity, may be used in accordance with the procedure of Example 9 for foaming with the multicomponent mixture described in that Example. If the reaction mixture is not cooled and merely left to react for another 45 minutes at 180° C, another 14 liters of $CO_2$ ar released through rapid carbodiimide formation, leaving a highly crosslinked, readily pulverizable foamed polycarbodiimide-group-containing solid with an NCO content of approximately 13%. The readily pulverizable product is highly crosslinked, modified, powdered biuret-carbodiimide-polyisocyanate with an extremely high proportion of free NCO groups and is a good adsorbent for fixing ammonia, methylamine, hydrazine and diamine vapors from industrial exhaust gases.

B. 26 parts by weight of the multicomponent mixture of 1 mol of ε-caprolactam, 1 mol of trimethylol propane, 1 mol of water and 1 mol of o-phosphoric acid are added dropwise with thorough stirring (1000 r.p.m.), over a period of 2.8 hours at 100° C, to 522 parts by weight of a commercial-grade tolylene diisocyanate (48.1% NCO, 2,4- : 2,6-isomer ratio 80 : 20). After 2 hours, measurement of the amount of $CO_2$ gas given off shows that approximately 3.6 liters of $CO_2$ had been released. The calculated quantity of $CO_2$ by biuret formation from the added water component of the multicomponent associate mixture is approximately 1.53 liters of $CO_2$. The increase of $CO_2$ of 2.07 liters (3.6–1.53) is attributable to substantially quantitative polyphosphate and phosphoric acid formation. The ε-caprolactam-modified biuret urethane polyisocyanate solution in the monomeric tolylene diisocyanate mixture is found to have an NCO content of 42.6%. If this solution is heated briefly for 1 hour to 180° C, vigorous decarboxylation takes place in addition to allophanatization of the polyisocyanate solution by catalysis of the unknown polycondensation and polyaddition products formed from phosphoric acid, another 14.1 liters of $CO_2$ being released over a short period. A highly viscous polyisocyanate-polycarbodiimide solution with an NCO content of 29.5% NCO is obtained. Catalysts with a strong catalytic effect on carbodiimide formation are thus obtained in situ during this reaction. The viscous ε-caprolactam-modified allophanate-biuret polyisocyanate mixture containing carbodiimide groups and 29.5% of NCO may be used in accordance with the procedure of Example 9 for foaming with multicomponent mixtures containing phosphoric acid.

EXAMPLE 32

(Comparison test)

If the reactions of Examples 31 (A) and (B) are carried out in the same way in the absence of ε-caprolactam (a) with water or (b) with water and phosphoric acid, the only reaction obtained are known biuret-forming reactions, in which the degree of biuret formation is determined by the water component and the evolution of carbon dioxide is determined by the quantity of water added.

EXAMPLE 33

A solution of 80 parts by weight of styrene, 20 parts by weight of methacrylic acid-β-hydroxypropyl ester and 0.8 parts by weight of azodiisobutyronitrile, is added dropwise, over a period of 4 hours at 120° C, to the multicomponent mixture of 1 mol of ε-caprolactam, 1 mol of 2-ethyl-1,3-hexane diol, 0.5 mol of water and 0.5 mol of orthophosphoric acid. Copolymerization is completed by heating for another 4 hours at 120° C. A multicomponent mixture containing relatively high molecular weight copolymers containing hydroxyl groups is obtained. The mixture may be foamed with polyisocyanates in a smooth reaction in accordance with the procedures of Example 9.

What is claimed is:

1. Low viscosity storable multicomponent mixtures comprising:
   a. at least one lactam-type compound,
   b. at least one acid group-free material, selected from the group consisting of:
      i. water
      ii. difunctional organic compounds containing functional groups selected from the group consisting of hydroxyl, primary amino, secondary amino and sulfhydryl, and
      iii. mixtures thereof,
   c. at least one organic or inorganic acid selected from the group consisting of:
      i. mono or polycarboxylic acid,
      ii. organic and inorganic acids of phosphorus
      iii. inorganic acids of boron, and
      iv. partially hydrolyzed antimonous and antimonic acid esters of polyhydroxyl compounds with molecular weights of from 62 to 600, wherein from 0.5 to 8 mols of component (b) and from 0.5 to 10 mols of component (c) are present per mol of component (a).

2. The mixtures of claim 1 wherein component (a) is selected from the group consisting of lactams, azalactams and mixtures thereof, component (b) is selected from the group consisting of
   i. water,
   ii. difunctional organic compounds containing functional groups selected from the group consisting of hydroxyl, primary amino, secondary amino, and sulfhydryl, and
   iii. mixtures thereof, and component (c) is selected from the group consisting of
   i. mono- and poly-carboxylic acids,
   ii. organic and inorganic acids of phosphorous,
   iii. inorganic acids of boron, and
   iv. partially hydrolyzed antimones and antimonous acid esters of polyhydroxyl compounds with molecular weights of from 62 to 600.

3. The mixtures of claim 2 containing caprolactam as component (a).

4. The mixtures of claim 2 containing as component (b) a polyol corresponding to the formula:

$$R(OH)_n$$

wherein

R represents a $C_2$–$C_6$ aliphatic hydrocarbon radical optionally interrupted by ether oxygen atoms; and n is either 2 or 3.

5. The mixtures of claim 2 containing phosphorous acid as component (c).

6. The mixtures of claim 2 containing o-phosphoric acid as component (c).

7. The mixtures of claim 2 containing boric acid as component (c).

8. The mixtures of claim 2 containing an olefinically unsaturated carboxylic acid as component (c).

9. The mixtures of claim 2 containing a hydroxy-carboxylic acid as component (c).

10. The mixtures of claim 2 containing formic acid as component (c).

11. The mixtures of claim 1 wherein component (a) is selected from the group consisting of lactams, azalactams, and mixtures thereof.

12. A process for the production of low viscosity storable multicomponent mixtures comprising mixing the following components at from 10° to 80° C:

a. at least one lactam compound,
b. at least one acid group-free material, selected from the group consisting of:
   i. water,
   ii. difunctional organic compounds containing functional groups selected from the group consisting of hydroxyl, primary amino, secondary amino and sulfhydryl, and
   iii. mixtures thereof;
c. at least one organic or inorganic acid selected from the group consisting of:
   i. mono or polycarboxylic acid,
   ii. organic and inorganic acids of phosphorous,
   iii. inorganic acids of boron, and
   iv. partially hydrolyzed antimonous and antimonic acid esters of polyhydroxyl compounds with molecular weights of from 62 to 600, wherein from 0.5 to 8 mols of component (b) and from 0.5 to 10 mols of component (c) are present per mol of component (a).

13. The process of claim 12 wherein component (a) is selected from the group consisting of lactams, azalactams and mixtures thereof.

* * * * *